(12) United States Patent
Fedder et al.

(10) Patent No.: US 10,292,656 B2
(45) Date of Patent: May 21, 2019

(54) FABRICATION FOR ULTRA-COMPLIANT PROBES FOR NEURAL AND OTHER TISSUES

(71) Applicant: CARNEGIE MELLON UNIVERSITY, a Pennsylvania Non-Profit Corporation, Pittsburgh, PA (US)

(72) Inventors: Gary K. Fedder, Turtle Creek, PA (US); Burak Ozdoganlar, Sewickley, PA (US); Peter J. Gilgunn, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 234 days.

(21) Appl. No.: 14/962,016

(22) Filed: Dec. 8, 2015

(65) Prior Publication Data

US 2016/0128636 A1 May 12, 2016

Related U.S. Application Data

(62) Division of application No. 13/680,794, filed on Nov. 19, 2012, now Pat. No. 9,241,651.

(Continued)

(51) Int. Cl.
*A01B 5/00* (2006.01)
*H01L 21/50* (2006.01)
(Continued)

(52) U.S. Cl.
CPC .......... *A61B 5/6848* (2013.01); *A61B 5/0478* (2013.01); *A61B 5/685* (2013.01);
(Continued)

(58) Field of Classification Search
CPC ...... A61N 1/05; A61N 1/0529; A61N 1/0534; B29C 35/02; B29C 35/0805; B29C 2035/0827; B29C 41/04; B29C 41/042; B29C 41/045; B29C 41/20; B29C 41/42; B29L 2031/753; B29K 2001/08; B29K 2995/006; B29K 2907/00; Y10T 29/49194; Y10T 29/49197; Y10T 29/49826;
(Continued)

(56) References Cited

U.S. PATENT DOCUMENTS

| 2001/0023367 A1* | 9/2001 | King | A61N 1/05 607/117 |
| 2003/0012884 A1* | 1/2003 | Pahl | H01L 21/50 427/407.1 |

(Continued)

FOREIGN PATENT DOCUMENTS

JP 2010089429 A * 4/2010

*Primary Examiner* — A. Dexter Tugbang
(74) *Attorney, Agent, or Firm* — David G. Oberdick; Michael G. Monyok

(57) ABSTRACT

Methods of fabricating ultra-miniature, ultra-compliant probe arrays through spin coating, wherein a dissolvable material in hydrogel form is dispensed onto an assembled mold with wires. Once the dissolvable material is dispensed onto the mold, centrifuging spin casts the material by evaporating the solvent, forming a dried dissolvable polymer. Finally, a device is used with water to remove excess dissolvable material to obtain a dissolvable needle with wires.

7 Claims, 40 Drawing Sheets

Related U.S. Application Data

(60) Provisional application No. 61/629,373, filed on Nov. 17, 2011.

(51) Int. Cl.

| | |
|---|---|
| *A61B 5/00* | (2006.01) |
| *A61B 5/0478* | (2006.01) |
| *A61N 1/05* | (2006.01) |
| *B29C 41/04* | (2006.01) |
| *B29C 35/02* | (2006.01) |
| *B29C 35/08* | (2006.01) |
| *B29C 41/20* | (2006.01) |
| *B29C 41/42* | (2006.01) |
| *G03F 7/00* | (2006.01) |
| *B29K 1/00* | (2006.01) |
| *B29L 31/00* | (2006.01) |

(52) U.S. Cl.
CPC ............ *A61N 1/05* (2013.01); *A61N 1/0529* (2013.01); *A61N 1/0534* (2013.01); *B29C 35/02* (2013.01); *B29C 35/0805* (2013.01); *B29C 41/04* (2013.01); *B29C 41/042* (2013.01); *B29C 41/045* (2013.01); *B29C 41/20* (2013.01); *B29C 41/42* (2013.01); *G03F 7/0035* (2013.01); *H01L 21/50* (2013.01); *A61B 2562/028* (2013.01); *A61B 2562/046* (2013.01); *A61B 2562/125* (2013.01); *A61B 2562/222* (2013.01); *B29C 2035/0827* (2013.01); *B29K 2001/08* (2013.01); *B29K 2907/00* (2013.01); *B29K 2995/006* (2013.01); *B29L 2031/753* (2013.01); *Y10T 29/49194* (2015.01); *Y10T 29/49197* (2015.01); *Y10T 29/49826* (2015.01)

(58) Field of Classification Search
CPC ..... H01L 21/50; A61B 5/0478; A61B 5/6848; A61B 5/685; A61B 2526/028; A61B 2526/046; A61B 2526/125; A61B 2526/222; G03F 7/0035
See application file for complete search history.

(56) References Cited

U.S. PATENT DOCUMENTS

| | | | |
|---|---|---|---|
| 2009/0099441 A1* | 4/2009 | Giszter | A61N 1/0529 |
| | | | 600/377 |
| 2016/0136928 A1* | 5/2016 | Zhao | B05D 1/005 |
| | | | 428/339 |

* cited by examiner

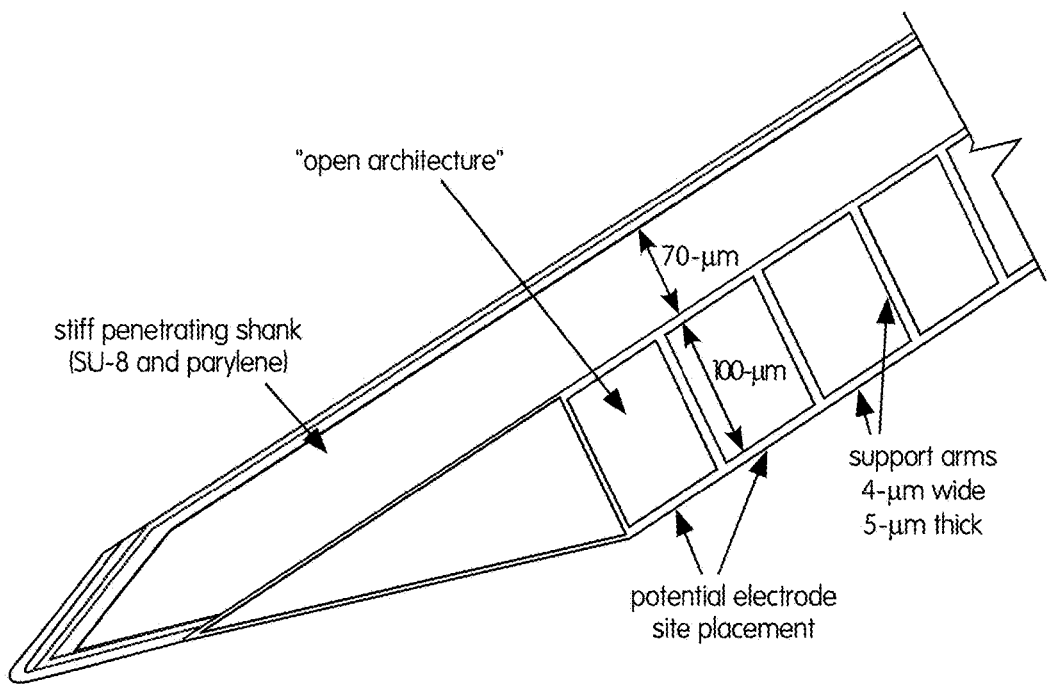
Prior Art
Fig. 3A
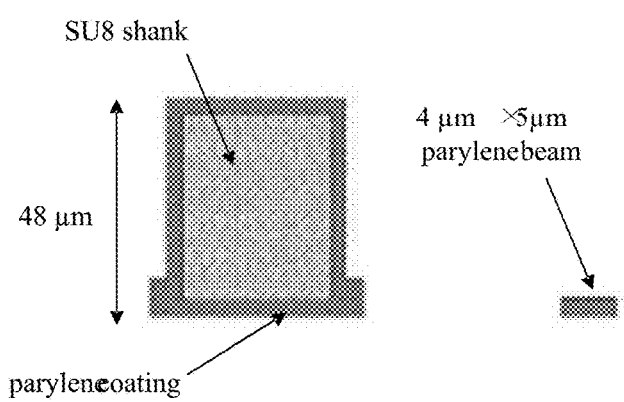
Prior Art
Fig. 3B
Prior Art
Fig. 3D

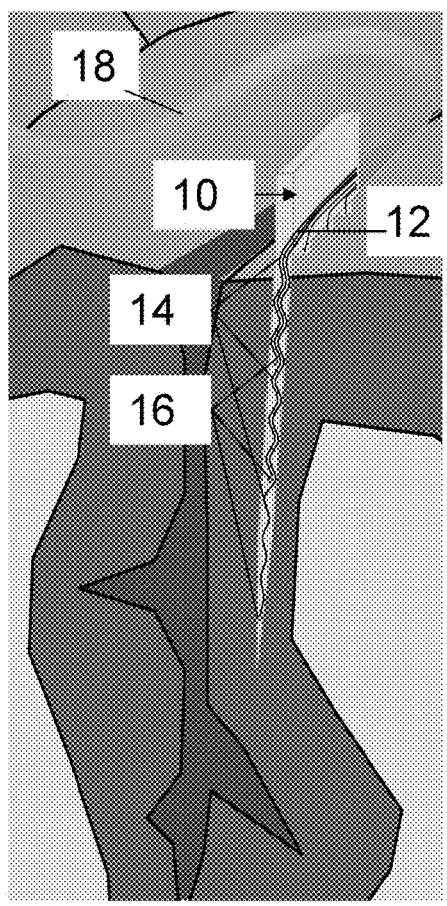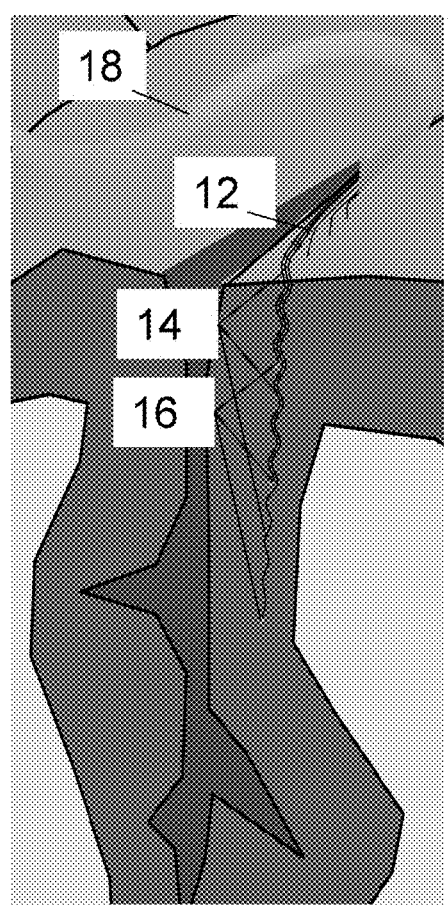
Fig. 4B                    Fig. 4C

FABRICATION FOR ULTRA-COMPLIANT PROBES FOR NEURAL AND OTHER TISSUES

CROSS-REFERENCE TO RELATED APPLICATIONS

The present invention is a Divisional Application of U. S. Non-Provisional application Ser. No. 13/680,794, filed Nov. 19, 2012 which claims priority from U.S. Provisional Application 61/629,373, filed Nov. 17, 2011, all of which are incorporated by reference herein.

STATEMENT REGARDING FEDERALLY-SPONSORED RESEARCH AND DEVELOPMENT

This invention was made with partial government support under The Defense Advanced Research Projects Agency (DARPA) grant number N66001-11-1-4025. The government has certain rights in this invention.

FIELD OF THE INVENTION

This invention relates to flexible electrodes and electrode arrays, and in particular to flexible electrode arrays that are useful for neural stimulation and recording, and methods of manufacturing the same. The present invention also covers the flexible electrodes and electrode arrays that could be used for applications in any human and animal tissues for the purpose of recording electrical signals or applying electrical stimulation. More particularly, the present invention describes high-compliance probes and their application for stimulation and recording from neural and other body tissues, and methods for manufacturing same. A specific aspect of the invention is the use of dissolvable, biodegradable, and biocompatible needles that encase the electrodes and facilitate their delivery into tissue.

BACKGROUND OF THE INVENTION

Research on neural-machine interfaces (NMI) in recent years has demonstrated the feasibility of driving motor prosthesis for the upper limbs. Neural interface reliability has been identified as a critical research area where progress is needed prior to transitioning NMI technology for practical restoration of motor function in humans. Two key issues are 1) the inability of current interfaces to reliably obtain accurate information from neurons over a period of decades, and 2) currently measured neural signals cannot be reliably used to control prostheses with high speed and resolution.

Neural probe hardware implanted in the brain tissue is a critical element in achieving these reliability goals. Failure of neural probes may be caused by several issues. After implantation, current probes are surrounded by reactive microglia and reactive astrocyte scarring as shown pictorially in FIG. 1A. Tissue reaction with the probe results in encapsulation that insulates the electrode by impeding diffusion and may impede current flow. Encapsulation increases the distance of the electrode from active neurons. For viable recording, the distance of the electrode from active neurons must be less than 100 µm. Progressive death and degeneration of neurons in the zone around the inserted probe due to chronic inflammation may eliminate neural electrophysiological activity. Lastly, interconnects may fatigue and break due to stresses. Experiments in animals have resulted in some neural electrode sites failing while others keep working for several years. This variability in outcome is believed to be due to several factors including variable blood-brain barrier (BBB) damage, variable scar formation, mechanical strain from micromotion, inflammation, microglial condition and disconnected neurons.

Neural probes employed today for neural-machine interface studies are essentially stiff needles usually made from wires, silicon or glass. Metal wire neural probes are typically 50-100 µm in diameter and usually made of platinum or iridium and insulated with glass, Teflon, polyimide or parylene. Basic tests were performed in 1974 determining that iridium, rhodium, platinum and palladium, in that order, have excellent resistance to electrolysis under conditions simulating biostimulation applications Iridium appears best and microelectrodes should exhibit lifetimes against electrolysis of decades. 2D arrays of wire probes have been made for chronic implantation. Drawbacks of this approach are the manual assembly, the lack of multiple electrodes per shaft, and issues with the predominantly metal wire splaying when inserted in the tissue. FIG. 1B is a predicted outcome with the miniature, ultra-compliant probe according to the present invention.

Silicon probes made with MEMS fabrication were first introduced by Ken Wise and Jim Angell at Stanford in 1969. Ken Wise's group at the University of Michigan subsequently developed a series of silicon probes and probe arrays with multi-site electrodes. The Michigan probes are made through a wet etch step that stops on boron-doped Si and necks the shank thickness down to around 15 µm. In more recent work, Si Deep reactive-ion etching (DRIE) has been used to make Si probes without the boron etch stop.

A 2D probe array was developed at the University of Utah in 1991, known as the Utah Electrode Array (UEA). The shanks in the UEA are made by sawing grooves into the substrate followed by a silicon wet etch to smooth the sidewalls and sharpen the needles. Platinum is deposited on the needles, which are subsequently coated in polyimide with just the tip exposed. Iridium has also been used for metallization. The UEA has been demonstrated repeatedly to record chronically, has recording sites 50 to 100 µm long, suggesting to some researchers that large recording site sizes perform better for chronic recording.

Polycrystalline diamond (poly-C) probes with 3 µm thick undoped poly-C on a ~1 µm $SiO_2$ layer have been fabricated by Dr. Aslam's group at Michigan State University. These probes, 5 mm long, are capable of electrical and electrochemical recording with AgCl reference electrodes, Au counter electrodes and doped poly-C working electrodes.

Research groups have created more compliant probes made with thin-film wiring embedded in polymer insulating films. Flexible central nervous system (CNS) probes have been made in polyimide, SU8/parylene and all parylene. However, flexible probes for single-unit detection have had to maintain adequate stiffness for insertion into the brain tissue. Thus, all prior art probes are made with a straight shank and relatively large probe diameters. The result is that even the most advanced of today's probes are extremely stiff in both axial and transverse directions relative to brain tissue, which has a Young's modulus of approximately 30 kPa. Any axial force transmitted through the external cabling directly acts on the probe and creates shear forces at the electrode-tissue interfaces. Such forces may come from external motion or from tissue growth around the implant. A team from Drexel Univ., the Univ. of Kentucky and SUNY created ceramic-based multisite microelectrode arrays on alumina substrates with thickness ranging from 38 to 50 µm, platinum recording sites of 22 µm×80 µm, and insulation using 0.1 μm ion-beam assisted deposition of alumina. The 7 mm-long shanks widen to 700 μm at the base. Their experience has shown that if the electrode is implanted slowly, there is a greater likelihood of recording a single neuron and when implanted quickly single units could not be recorded. After 3 months, there were no clear single neuron recordings from any recording sites and subsequent immunohistology showed glial formation for several hundred microns beyond the insertion hole.

Y.-C. Tai's group at Caltech produced parylene-coated silicon probes with integral parylene cabling, shown in FIG. 2A. The shanks were up to 12 mm long. Parylene adhesion to silicon was enhanced by performing a short $XeF_2$ etch to roughen the substrate. A primary innovation was a flexible 10 μm-thick, 830 μm-wide, 2.5 mm-long parylene cable. Sacrificial photoresist was placed under the cable as a release layer. Backside Si DRIE was used to free the device from the rest of the substrate. A 200° C. anneal for 48 hr was performed to soften and allow straightening of the meanders in the cabling from the compact planar layout. 16-channel Omnetics connectors were bonded with conductive epoxy in through-holes on the parylene and backed with a printed circuit board for mechanical strength.

Flexible polyimide probe arrays (FIG. 2C) have been made with gold electrodes. These probes must be inserted by first creating an insertion hole with a scalpel or needle. A later polyimide probe array incorporated silicon for selected locations along the length of the shank, with polyimide connectors to create enhanced compliance, as shown in FIG. 2B.

FIGS. 3A and 3B illustrated an all-polymer probe design incorporated a lateral lattice-like parylene structure attached to a larger SU8 shank to reduce the structural size close to the electrodes. The lattice structure, shown in FIG. 3A, included a 4 μm-wide, 5 μm-thick lateral beam (See FIG. 3D) located parallel to the main shank. Encapsulating cell density around the lateral beam was reduced by one-third relative to the larger shank. SU8 shank can be coated with a parylene coating forming a coated shank having a depth of 48 μm.

Flexible probes have been made in all parylene with 0.5 μm-thick gold interconnect and electrodes. The parylene cross-sectional dimension was set at 100 μm wide and 25 μm thick to create adequate stiffness for insertion. Probes up to 2.5 mm long, shown in FIG. 2D, were designed but insertion was performed to 0.5 mm. The probe retained mechanical and electrical integrity following acute tests in rats after controlled cortical impact with a 2 mm stroke. Researchers at IMTEK created ultra compliant ECoG probes on a polyimide/platinum foil substrate. The 252-channel array spanning 35 mm by 60 mm was made by spinning two 5 mm-thick polyimide films onto a silicon substrate. The first polyimide film was roughened by $O_2$ plasma to enhance adhesion of the direct sputtered 300 nm-thick platinum interconnect layer. Tweezers were used to pull the finished array from the wafer. Omnetics connectors were electrically bonded to through-holes in the film with solder paste and mechanically fixed with epoxy. QuinetiQ is developing liquid crystal polymer neural probes and cables. Rogers' group at UIUC has developed implantable electrodes using transfer of silicon parts onto bioresorbable silk with a Polydimethylsiloxane (PDMS) stamp process. This approach will prove useful for ECoG electrodes as well.

U.S. patent application Ser. No. 20090099441 from Dr. Giszter's Drexel group describes biodegradable stiffening wires 1 braided with electrode wires 2 with electrodes 3 (see FIG. 3C) where flexible wires 2 are braided onto a large diameter, stiff maypole structure 4 with stiff biodegradable strands 1. When the biodegradable strands 1 dissolve, the flexible wiring 2 is left in the brain tissue. Reliable and manufacturable connections to the braided wires become difficult when scaled to arrays.

Olbricht et al has reported on flexible microfluidic devices supported by biodegradable insertion scaffolds for convection-enhanced neural drug delivery. The device consists of a flexible parylene-C microfluidic channel that is supported during its insertion into tissue by a biodegradable poly(DL-lactide-co-glycolide) (PLGA) scaffold. The scaffold is made separately by hot embossing the PLGA material into a mold. The parylene-C microfluidic channel is then manually assembled by first tacking it down to the scaffold with a drop of epoxy followed by a dip in dichloromethane to partly dissolve some of the PLGA and thereby attach it to the parylene-C shank. The PLGA shanks were nearly 100% degraded after 27 days in organic chemical buffering agent and were compliant after 15 to 18 days.

Suzuki, Mabuchi et al, describe multichannel flexible neural probes coated with PLGA microspheres that were infused with nerve growth factor. Two types of neural probes were created. Both probe types included flexible thin-film parylene-C probes. The first probe (type-A) included a parylene-C groove along the shank for manual placement of PLGA microspheres mixed with polyethylene glycol. The second probe (type-B) included multiple electrodes without the groove structure. The PLGA was manually coated to create the biodegradable shank for insertion. Both probes were inserted in a rat cortex, with successful neural recording from the type-A probe. Neural signals were not observed from the type-B probe, presumably due to residual PLGA obstructing the electrode.

Tyler et al, have developed a neural probe made from a polymer nanocomposite of poly(vinyl acetate) (PVAc) and tunicate whiskers, inspired by the sea cucumber dermis. The probe material exhibits a real part of the elastic modulus (tensile storage modulus) of 5 GPa after fabrication. When exposed to physiological fluid conditions, its modulus decreases to 12 MPa. The probe did not include wiring. Results from animal implantation studies showed an increased neuronal density and decreased glial formation around the PVAc probe when compared to a 50 μm-diameter tungsten wire probe. This work provides evidence that mechanical flexibility of the probe is an important aspect of reliable neural probes.

SUMMARY OF THE INVENTION

This present invention describes methods, systems and apparatuses of ultra-miniature, ultra-compliant probe arrays, and associated biodissolvable and/or biodegradable delivery vehicles. Although the present invention finds applications in many human and animal tissue systems, as a specific focus and example, the application of ultra-compliant probes and probe arrays to intracortical neural probing is described here. The probe array allows design flexibility to match the stiffness of the tissue it is being applied to, such as the brain tissue, in all three axes (x, y and z), with interconnect cross section (thickness and width) smaller than cell dimensions (<10 μm). This stiffness matching requires specific geometric and fabrication approaches, commonly leading to ultra-thin probe wires. This invention also allows the sizing of the electrodes for specific cell dimensions, e.g., to reduce glial scar formation. Further enhancement of compliance is obtained by incorporating different geometric features to the electrode, such as meandering the electrode wires. The small thickness and geometric features of the wires commonly result in very high compliance (as required). Under these circumstances, to enable effective insertion of the probes to the tissue (e.g., brain), the present invention uses stiff biodisolvable and/or biodegradable polymers, including (but not limited to) single use or combinations of carboxymethyl cellulose (CMC), polyvinylpyrrolidone (PVP), polyvinyl alcohol (PVA), maltose, other sugar molecules, polylactic acid (PLA) and its co-polymers. Furthermore and importantly, drugs, such as dexamethasone, and other biologics can be embedded into the biodegradable polymers to realize effects, such as anti-inflammation, during the application.

Distinguishing features of the present invention are (1) the use of specific electrode thickness (thin electrodes) that are sized for particular tissues and cells, as well as for tailored compliance, (2) the use of specific electrode geometries, such as meandered electrodes, to further increase the compliance in the axial and lateral directions, (3) the use of biodegradable and/or bio-dissolvable polymers (e.g., CMC) that create a stiff enclosure to the electrodes, thereby facilitating their reliable insertion; as well as reducing or eliminating permanent tissue damage by rapidly dissolving, (4) specific geometric features on the polymer needles that enable reduced tissue damage (e.g., micro-scale dimensions), easier insertion (e.g., sharp edges), retention (e.g., negative angles or undercuts), and mechanical stability (e.g., fillets), (5) capability to incorporate additional bio-agents and drugs into the needle material to enable specific biological response (e.g., dexamethasone to reduce inflammation), and (6) the ability to batch fabricate the probes with planar processing, making the probes less expensive and more repeatable, especially when scaled to multi-site multi-probe arrays.

Many other applications of electrodes and electrode arrays for providing stimulation and gathering electrical signals (e.g., to/from cardiac tissue, muscle tissues, etc.) have been considered. Those applications will also benefit from specifically sized (with respect to the cell dimensions) and compliance matched electrodes and electrode arrays that will provide minimal-to-no tissue damage, longevity, and reliability: they are also covered in this invention.

BRIEF DESCRIPTION OF THE DRAWINGS

FIGS. 3A-D shows prior art probe arrays;
FIGS. 4A-C show schematics of a probe array according to the present invention.

DETAILED DESCRIPTION OF THE INVENTION

This present invention describes methods, systems and apparatuses of ultra-miniature, ultra-compliant probe arrays. Although the present invention finds applications in many human and animal tissue systems, as a specific focus and example, the application of ultra-compliant probes and probe arrays to intracortical neural probing is described here. The probe array allows design flexibility to match the stiffness of the tissue it is being applied to, such as the brain tissue, in all three axes (x, y and z), with interconnect cross section smaller than cell dimensions (<10 µm). This stiffness matching requires specific geometric and fabrication approaches, commonly leading to ultra-thin wires. This invention also allows the sizing of the electrodes for specific cell dimensions, e.g., to reduce glial scar formation. Further enhancement in compliance is obtained by incorporating different geometric features to the electrode, such as meandering the electrode wires. The small thickness and geometric features of the wires commonly result in very low stiffness (as required). Under these circumstances, to enable effective insertion of the probes to the tissue (e.g., brain), the present invention uses stiff bio-disolvable and/or biodegradable polymers, including (but not limited to) single use or combinations of carboxymethyl cellulose (CMC), polyvinylpyrrolidone (PVP), polyvinyl alcohol (PLA) and its co-polymers. The descriptions below consider specifically CMC as the material of choice, but the invention is not limited to the use of CMC, but covers the use of any bio-dissolvable and bio-degradable polymer that encases the electrodes to facilitate the insertion. Furthermore, the invention covers different geometries of the polymer (insertion) needles, such as sharp tips, serrated edges, fillets (for increased mechanical stability), to name a few.

Figure 1A:
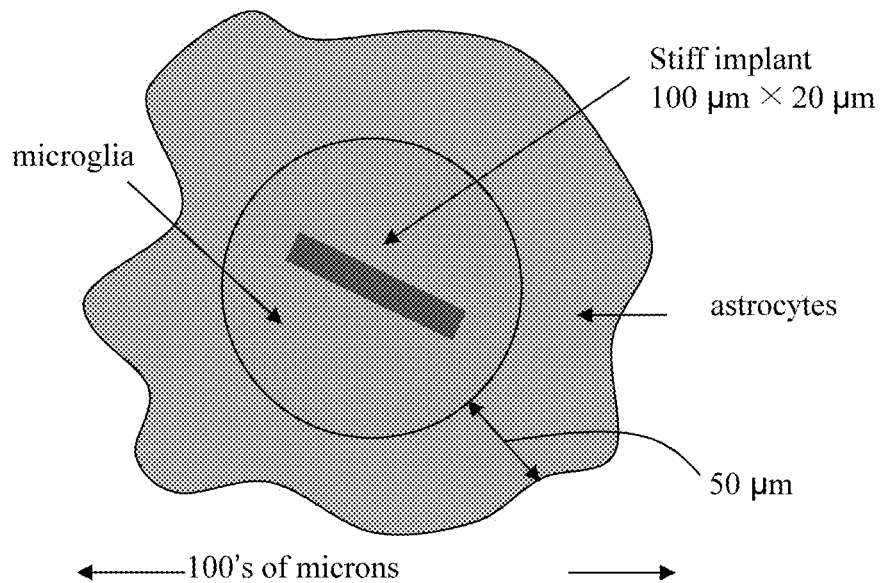
FIGS. 1A and 1B show schematics of tissue reaction to prior art neural probes.
Figure 1B:
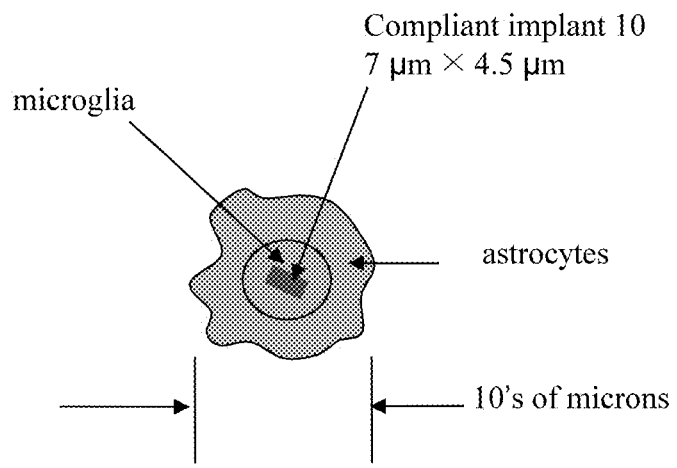
Figure 2A:
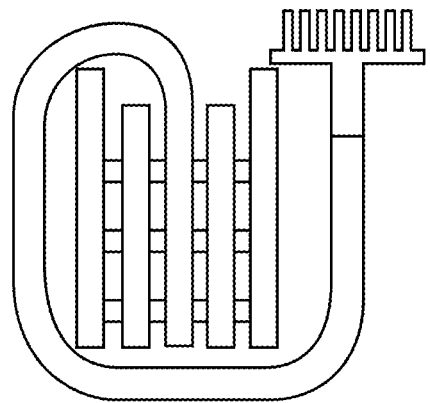
FIGS. 2A-D show prior art probe arrays.
Figure 2B:
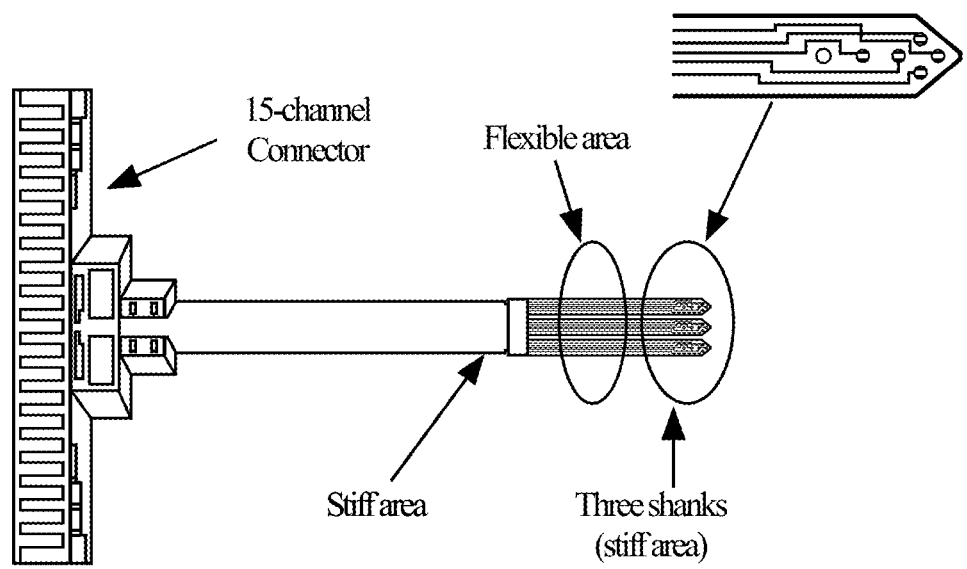
Figure 2C:
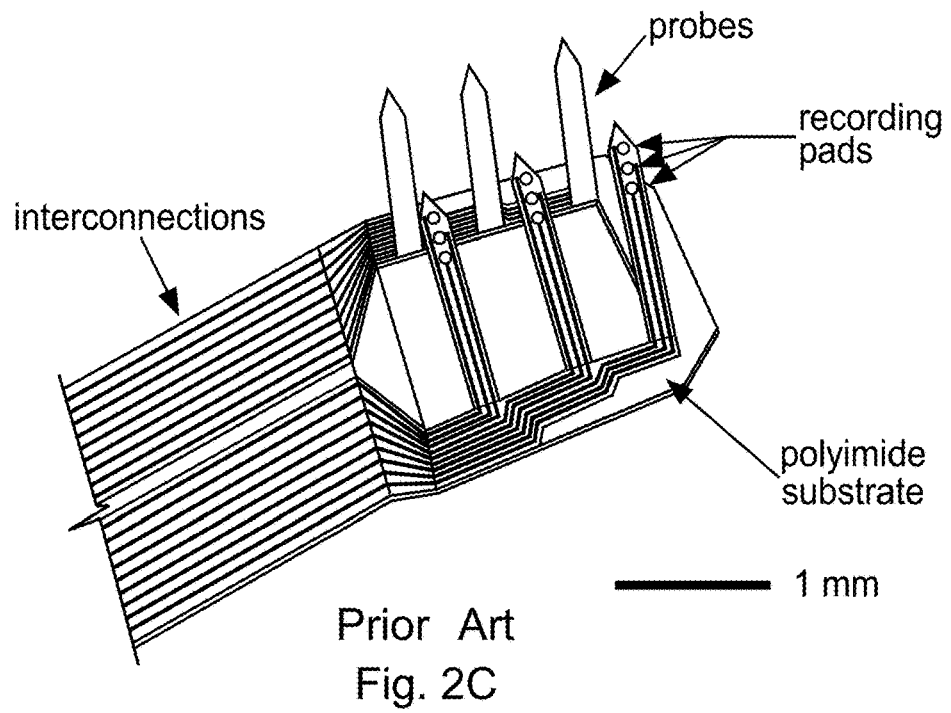
Figure 2D:
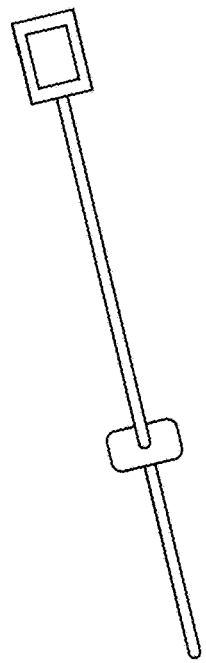
Figure 3C:
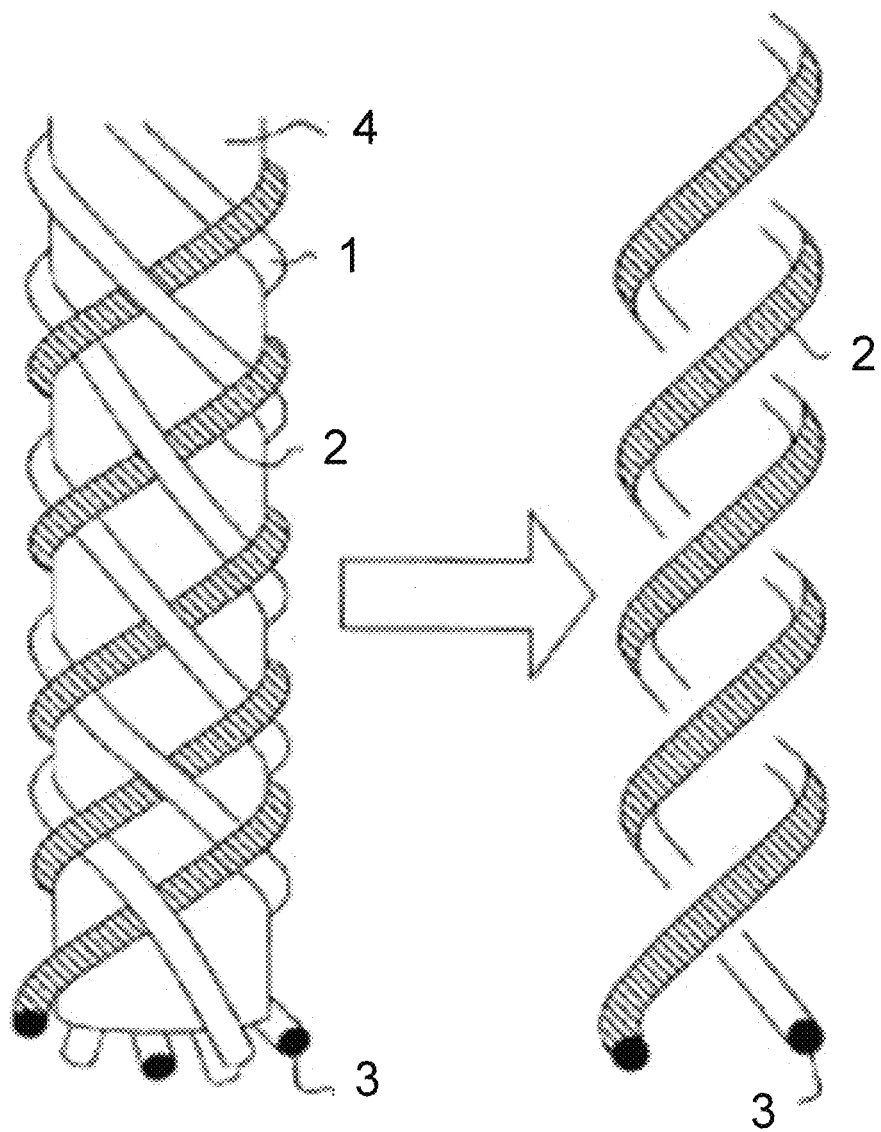
Figure 4A:
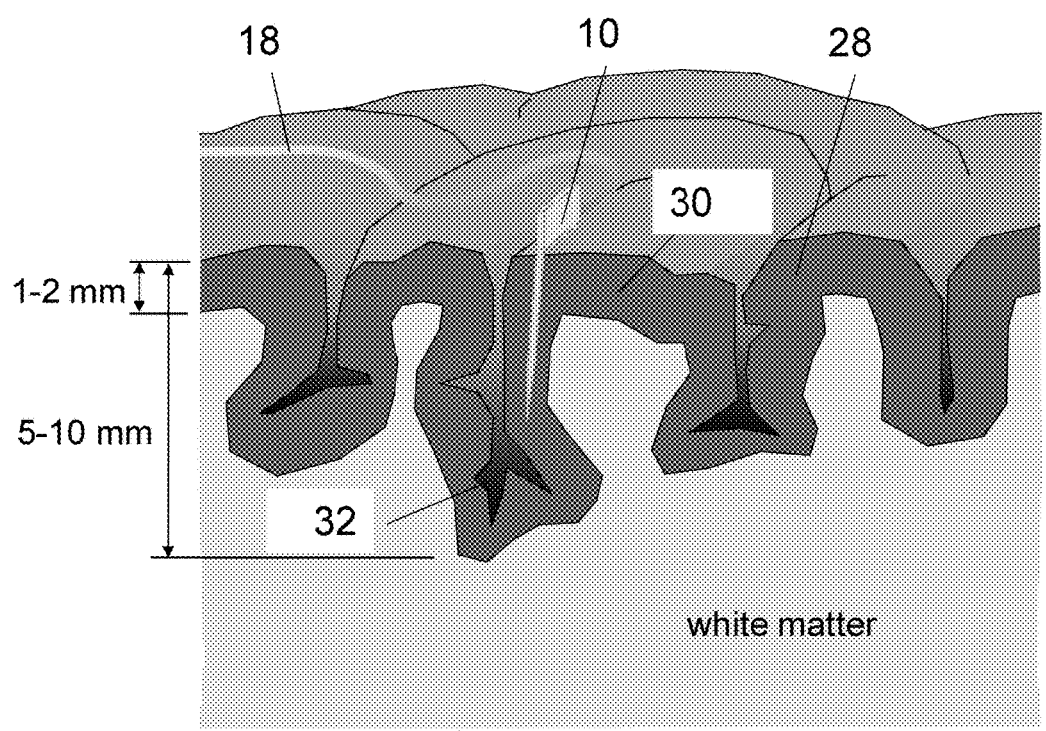

The concept of the probe array of the present invention 10 is illustrated in FIGS. 4A-C. The probes 10 are made from thin-film meandered platinum wiring surrounded by parylene-C (other polymers may be used). In contrast to prior flexible probes, the meandered wiring is compliant in the axial direction as well as in lateral directions. Wiring continues onto an integral parylene cable 12 to move connections away from the probe. The parylene cable 12 is designed to allow suturing or other attachment to the dura (or to the skin in the acute tests on small animals).

Figure 6:
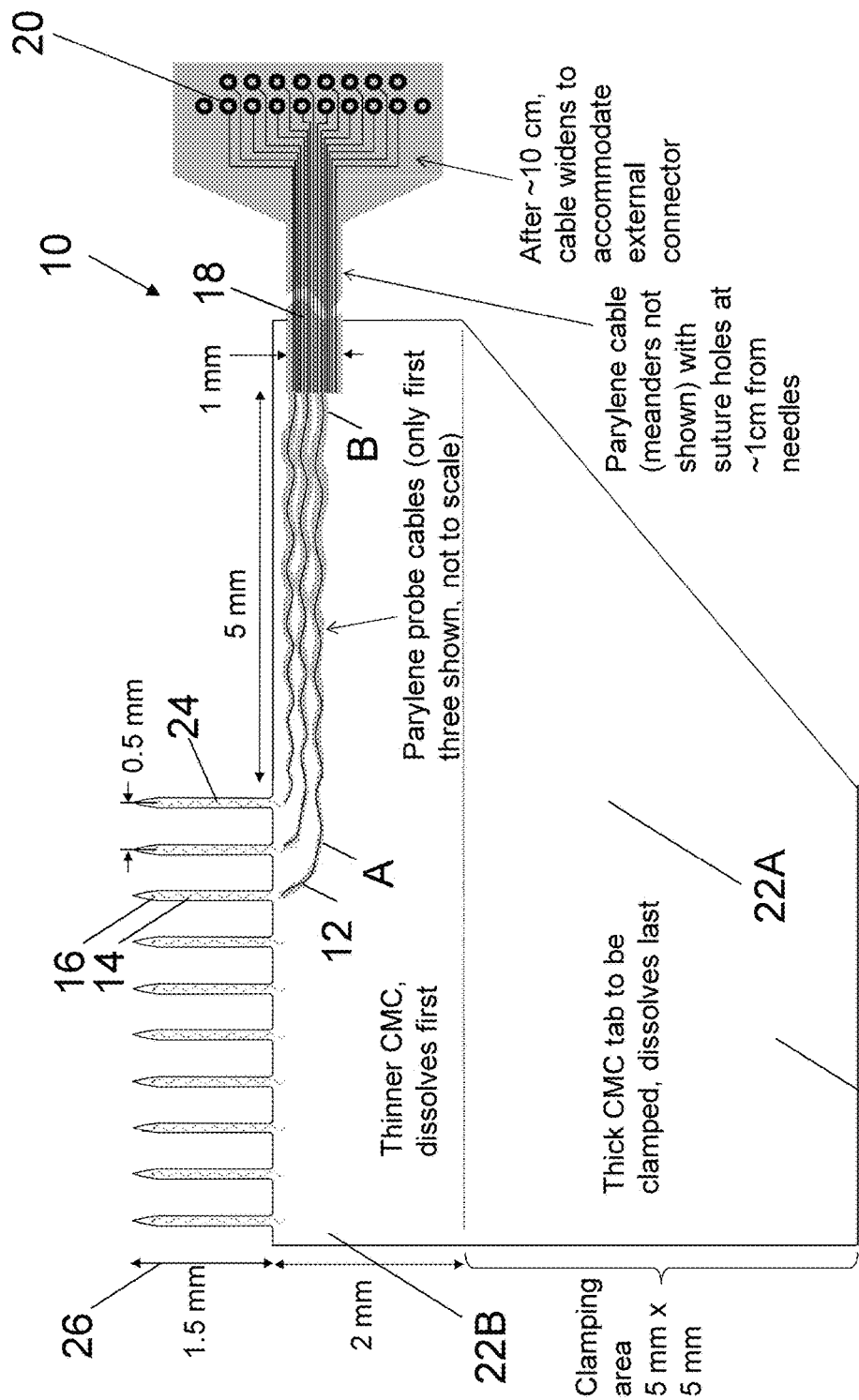
FIG. 6 shows a schematic plan view of the probe cabling according to the present invention.
Figure 7A:
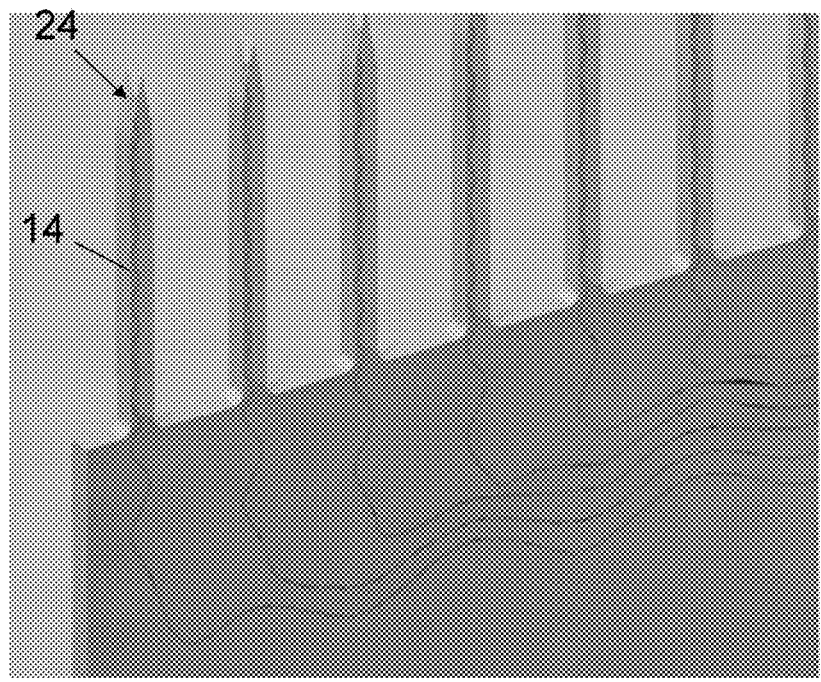
FIGS. 7A-C show solid model views of embodiments of the probes according to the present invention.

A schematic plan view of an envisioned probe array and cabling design is shown in FIG. 6. Wiring 14 coming out from the electrodes 16 is routed to the side to lie down naturally onto tissue. The individual parylene micro-cables 12 gradually widen from 7 µm (location A) to 40 µm (location B) while meandering to decouple stress from the main cable 18. After 5 mm, the wiring 14 is mechanically brought together onto a single integral parylene cable 18 that will span up to 10 cm. The wiring 14 is routed to a set of through-hole pads 20 with layout geometry that matches male connectors (not shown) used in neural recording hardware, such as Omnetics Nano NPD. A carboxymethyl cellulose (CMC), which is a fast degrading, non-cross-linked natural polymer, tab 22 is included to provide an attachment region for the stereotaxis micromanipulator that is used to manually insert electrodes into animals for the in vivo use. This technique provides a controlled and repeatable insertion for single probes and 1D array probes. The present invention is not restricted to the particular dimensions described. A multitude of designs with wiring of different length, width, thickness and orientation, with electrodes of different numbers, size and location, and with needle arrays of different numbers, size and shape. One embodiment of tab 22 includes two sections: a first section 22A that is thicker than a second section 22B such that the second section 22B dissolves before the first section 22A. One or more needle molds 24 are attached to the second section 22B. The probe wiring 14 is encased in the needle mold 24 of carboxymethyl cellulose (CMC). Use of blends of CMC with other biodegradable polymers, such as sucrose, glucose, maltodextrin, and poly(vinylpyrrolidone, PVP), is also possible to tune stiffness properties. The biodegradable needle temporarily supplies the necessary strength for insertion. Probe length 26 is dictated by the desire to place electrodes within the 1-3 mm thick grey matter 28 (see FIG. 4A) in the gyri 30, but to also access grey matter within the sulci folds 32 on the sides where large densities of motor neurons are located. The folds are up to 8 mm deep (e.g. in primates) and set an upper design limit on the probe length for most neural studies. Other probe lengths are possible and may be appropriate for deep brain stimulation, for example. FIG. 7A is an illustration of probe 10 having meandering wires 14 in each needle 24, wherein the meandering wires 14 are shown continuing into second section 22B of tab 22.

Sodium salt of carboxymethyl cellulose is categorized by the FDA as a "generally recognized as safe" substance. It has been used as replacement of silicon-based breast implants for over fifteen years and is being researched in direct contact with deep tissues for bone replacement/repair. CMC-alginate mixture-based injectable gels are currently being tested for the in situ formation of scaffolding for repairing CNS damage.

CMC has several distinct advantages over other biodegradable polymers, including (1) room-temperature preparation, which enables embedding bio-active agents directly into the material, (2) hydro-gel formability, which facilitates molding and spin-casting fabrication, (3) high strength and stiffness, providing required resistance for insertion application, (4) rapid bio-absorbability (dissolution), and (5) no harmful by-products from in vivo degradation. In contrast, PLA and PLGA require high-temperature preparation, and leave acidic by-products that prevent its usage for the needle application. However, depending on the specific tissue application, other biodegradable and dissolvable polymers may be utilized.

The effective stiffness of the CMC-encased probes depends not only on the mechanical properties of the CMC, but also the geometry of the needles. The fabrication conditions of the CMC, including viscosity of the initial hydrogel, molecular weight of the particular sodium-CMC used for fabrication, drying rate, and centrifuge conditions (for spin-casting) must be carefully controlled. Elastic modulus values between 0.7 GPa and 3 GPa can be expected, with tensile strength values between 14 MPa and 100 MPa. Given a set of material properties, the stiffness and effective strength of the needles depends on the needle geometry. Higher aspect ratios (length per diameter) will result in lower strength values. CMC can be blended with other biodegradable polymers to set particular stiffness and molding properties.

To obtain required strength and resistance to buckling and fracture during tissue insertion, the cross-sectional area in initial embodiments of the probes are approximately 100 µm×100 µm or 300 µm×100 µm. A small cross-section is desirable to limit damage to tissue upon insertion. The choice of cross-sectional area is dependent on adequate stiffness for insertion into tissue and probe length must be taken into account. Buckling can be predicted based on the end conditions and needle geometry and materials. Furthermore, enhancements to stiffness and factor-of-safety against failure can be attained in some embodiments by modifying the needle design (e.g., an I-beam design) without an increase in the cross-sectional area. The other factor affecting buckling is the maximum force required for the needle to penetrate the tissue. In some embodiments this is controlled by the needle design. The in-plane dimensions and shape are determined by the designed layout of the needle with one-to-one correspondence so characteristics like the radius of the needle tip and the tip angle can be modified to reduce the maximum force on the needle shaft during insertion. In other embodiments, the phenomenon of aspect ratio dependent etching (ARDE) allows control of the out-of-plane shape and dimension of the needle through the use of sacrificial patterns applied during the formation of the needle mold.

Figures 5A, 5B:
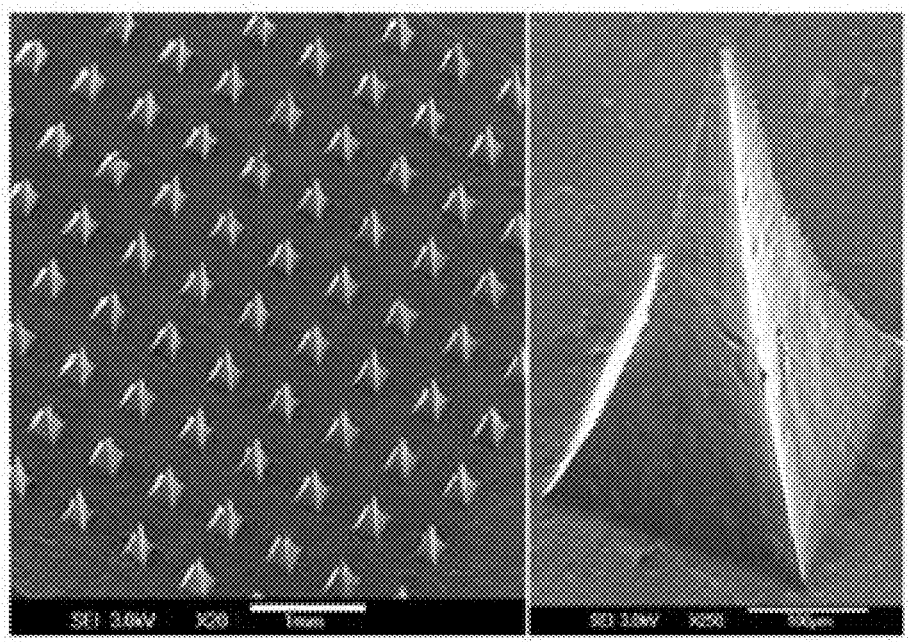
FIGS. 5A-E show SEM images of micromolded CMC needles before and after dissolution.
Figure 5C:
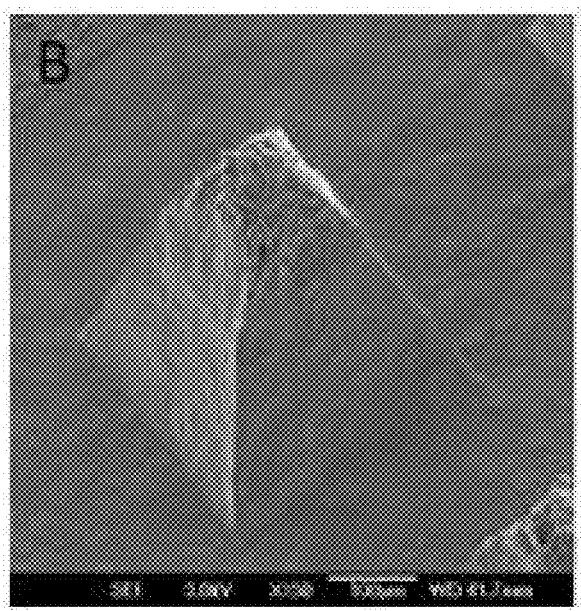
Figure 5D:
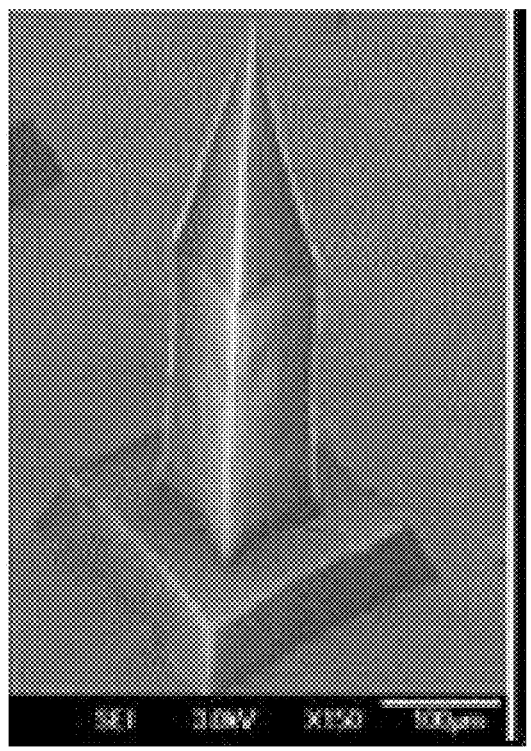
Figure 5E:
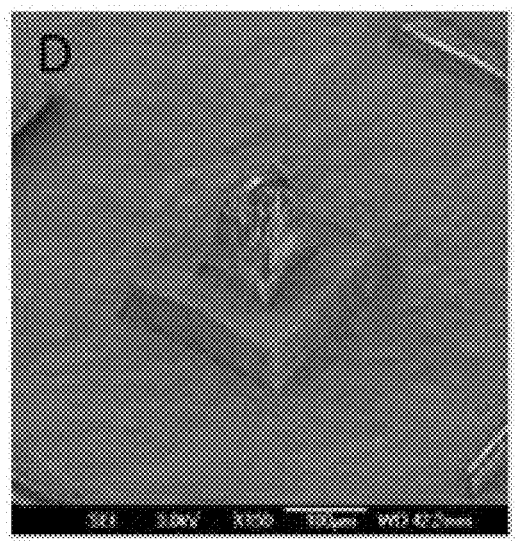

The strength against failure also depends on the stress concentrations. The inclusion of stress-concentration reducing features such as fillets can increase the strength of needles against fracture by an order of magnitude. Examples of micromolded CMC needles made by the inventors are shown in FIGS. 5A-E. The needles show a large amount of dissolution after insertion into human skin explants for 20 minutes (FIGS. 5C and E).

In some embodiments of the present invention, micro-molecules, macro-molecules, and/or particulates can be integrated into the dissolvable polymers (e.g., CMC) to provide additional functionalities or properties. For example, to mitigate the potential inflammatory response due to the insertion of the probes into the CNS, an anti-inflammatory drug, such as dexamethasone sodium phosphate, can be incorporated into CMC.

As another example, other biodegradable and/or non-degradable polymers can be added to the biodegradable polymer base to control/select the mechanical properties (stiffness, strength, etc.) and bio-degradability (dissolution rate) of the probe enclosures. For CMC base, some examples of added polymers include, but are not limited to, PVP, PVA, PLA, PLGA, and PCL. Furthermore, other complex sugars, such as maltose, dextrose, etc., can be added to the CMC matrix to control the needle characteristics. CMC's with different density can be mixed to attain improved dissolution properties. Further, deliberate porosity may be incorporated into CMC needles to accelerate dissolution rate.

Platinum provides low resistance interconnect, it is biocompatible, and it is widely used in neural probe electrodes. The conformal and inert nature of parylene-C is effective in sealing and insulating implantable electronics and wiring for short-term and medium-term use. Hermetic sealing layers, such as alumina or silicon carbide, are deemed important for long-term use. Ideally, the cross-section of the individual wires should be less than the surrounding neural cells; we are targeting an interconnect width including insulation layers of around 7 µm, which is a practical lower limit set by conventional contact photolithography. Smaller wiring width is possible with advanced lithography. Wiring becomes wider when brought onto the integral parylene cabling. The resulting wire resistance is on the order of 100Ω for a 1.5 mm probe.

Figure 9A:
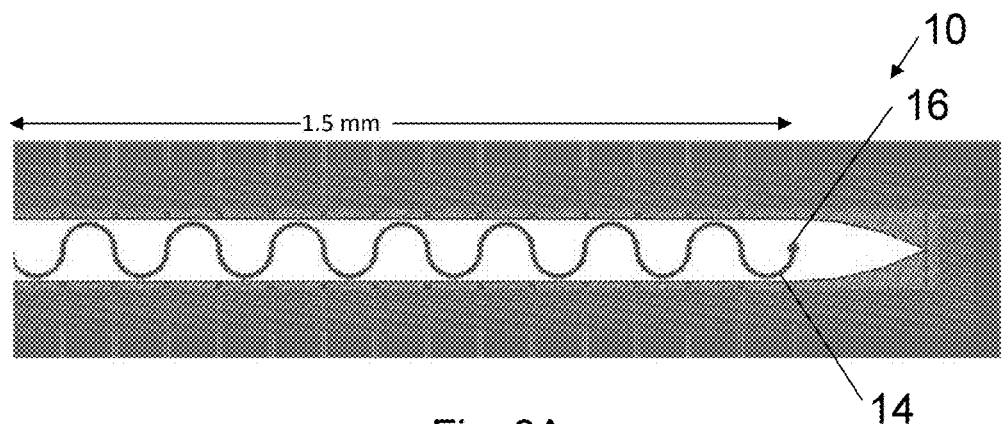
FIGS. 9A-C show plan view schematics of the layout of a single electrode made according to the present invention.
Figure 9B:
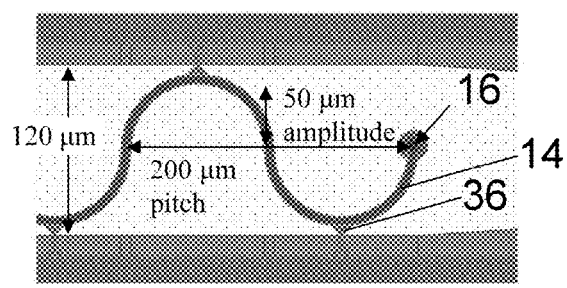

Now turning to FIG. 9B, a meander amplitude of 50 µm (i.e. the width of the meander pattern measured from its axis) results in axial compliance that is less than the tissue and will decouple external probe stress from the electrodes. In one embodiment, the meander is formed from circular arcs, which have lower stress concentrations than other curved shapes of similar amplitude and pitch leading to a design that is fundamentally more robust mechanically and less prone to fatigue failure modes during the continuous mechanical cycling characteristic of pulsatile and respiratory brain micromotion. Since the compliance in the lateral directions is more than two orders of magnitude smaller than the axial compliance, this amount of meandering may not be necessary, but underscores that there is plenty of room in the fabrication method to match the mechanical impedance of brain tissue. Many other designs of meandering geometries and sizes are possible. For example, meander designs can be zig-zag (triangular-wave) shaped, square-wave shaped, or many other periodic or aperiodic shape. Corners of the meanders can be rounded with various radius values. A probe of such large axial compliance could never be inserted without a stiff needle connected mechanically in parallel. Our biodegradable needle solution is effective for this purpose.

Figure 7B:
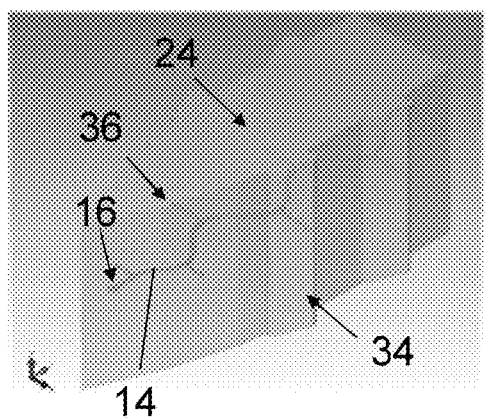
Figure 7C:
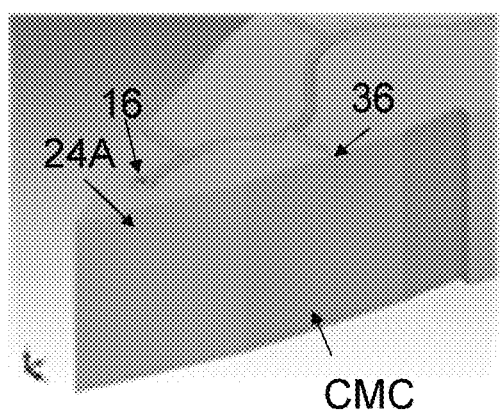
Figure 9C:
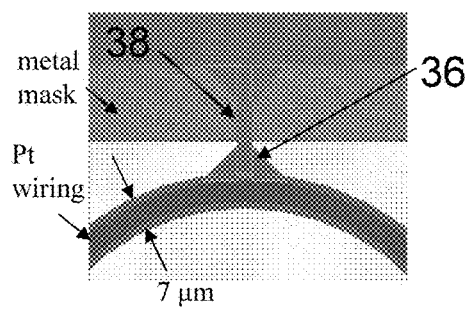
Figure 10A:
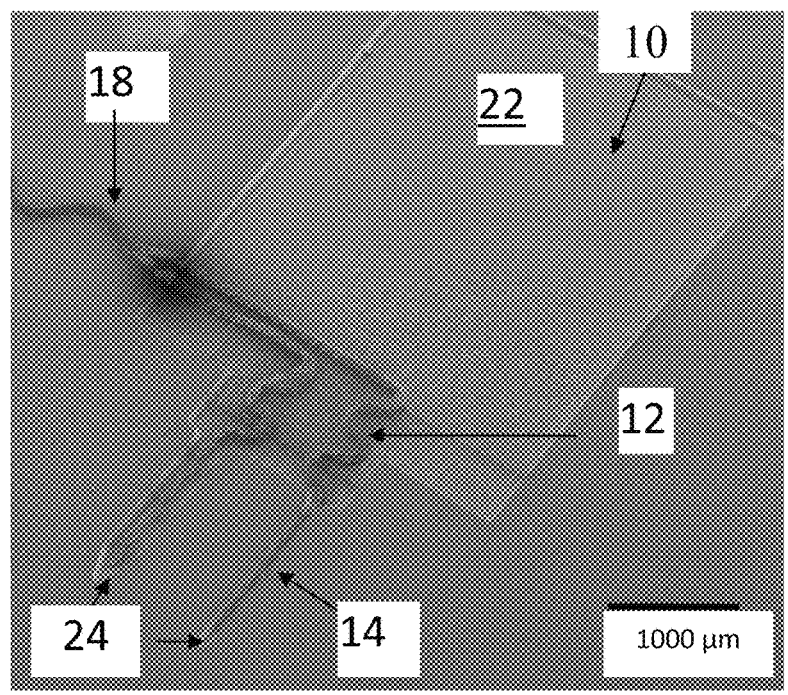
FIGS. 10A and 10B show the meandered wires and electrical output cables prior to encapsulation in a biodegradable and/or biodissolvable polymer.
Figure 10B:
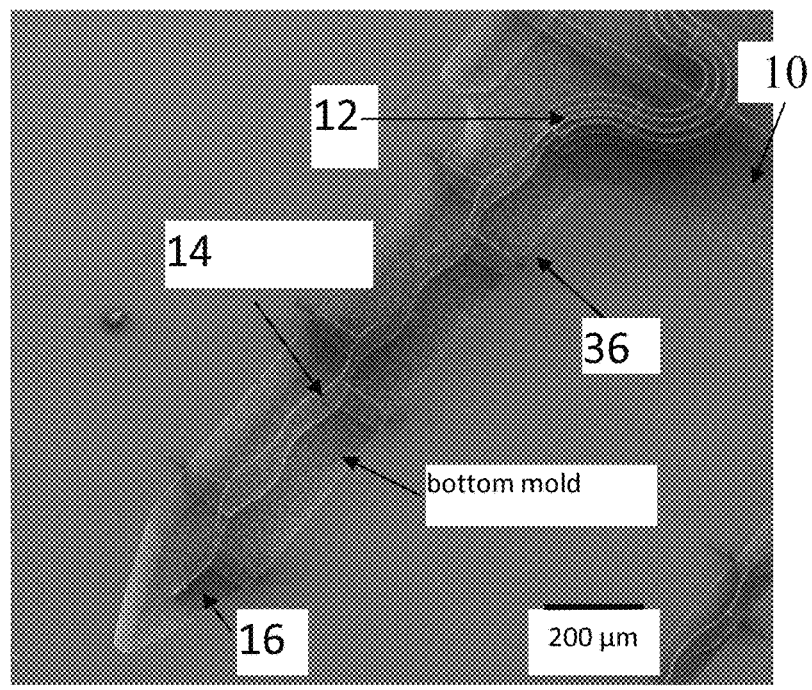
Figure 11:
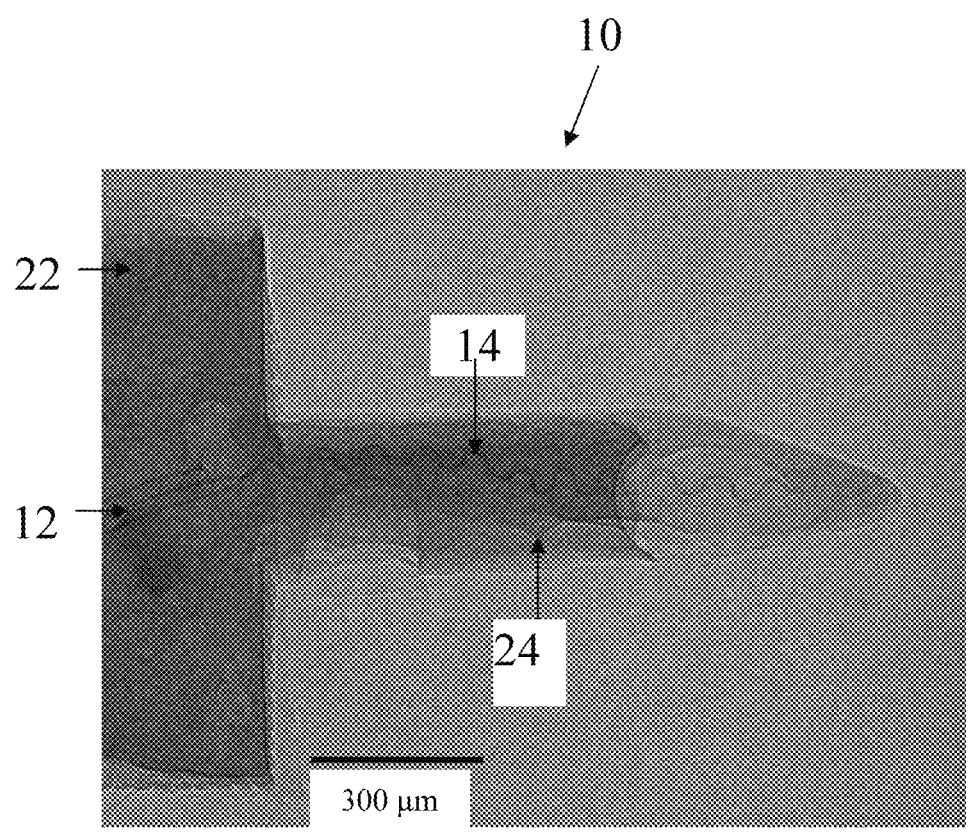
FIG. 11 shows an X-ray image of a single channel neural probe embedded in a biodissolvable polymer.
Figure 12A:
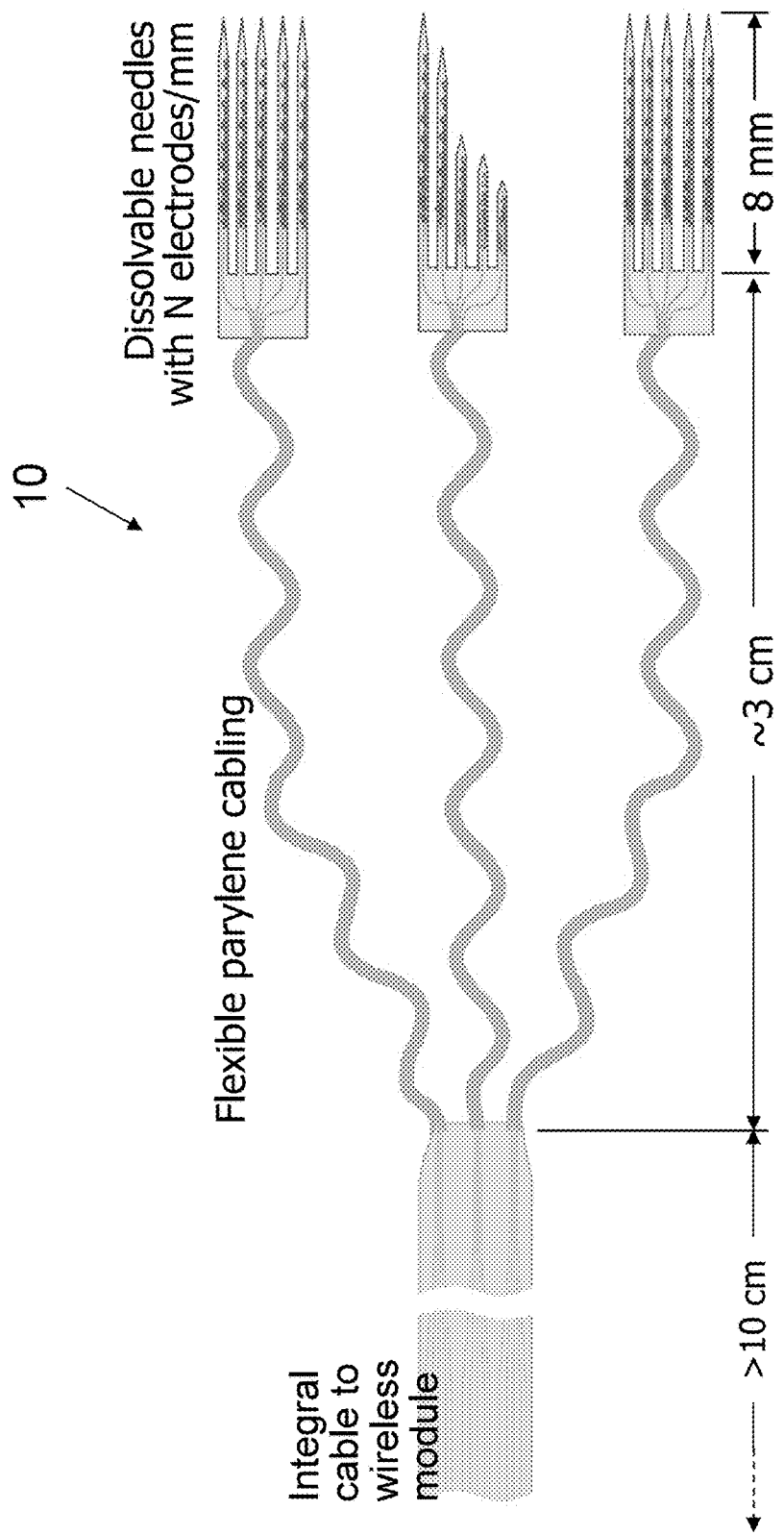
FIGS. 12A-B shows various embodiments of the present invention.
Figure 12B:
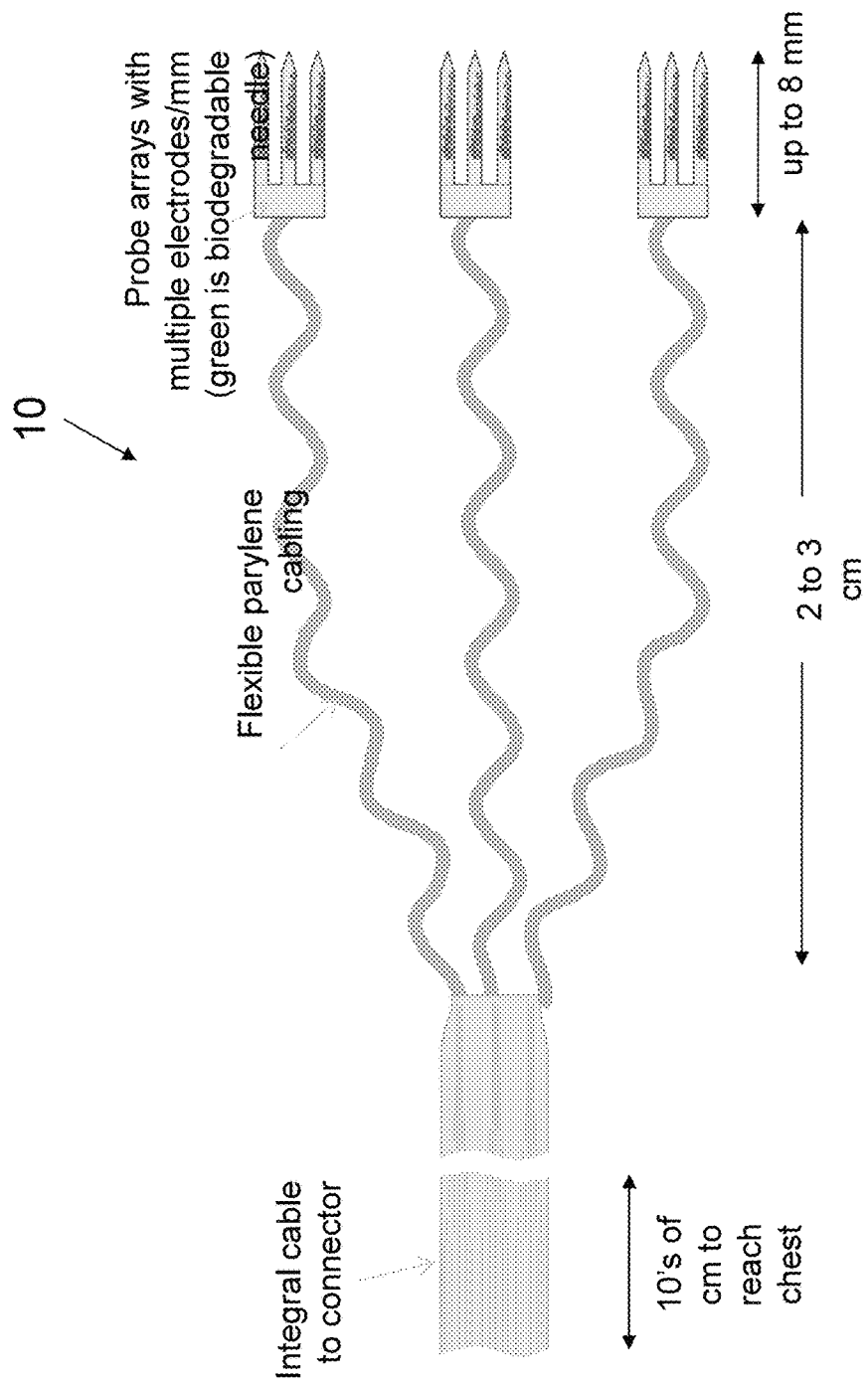

In one embodiment of the present invention, as shown in FIG. 7B, sidewall barbs 34 are cast into the CMC needle 24 to keep the needle 24 inserted in the tissue. Parylene tethers 36 hold the wiring 14 in place during the CMC molding (see FIGS. 9A-9C). Necking regions 38 of the tethers 36 (see FIG. 9C) will aid in breaking. The wiring 14 meanders as shown have an amplitude of about 25 µm. These meanders provide the low axial and lateral compliance that is unique to our design. Now turning to FIGS. 9A-C illustrating an embodiment for 4.5 µm-thick, 7 µm-wide, 1.5 mm long parylene electrode wiring 14 with 50 µm amplitude and 200 µm pitch meanders and assuming E=2.76 GPa, the axial spring constant is 0.35 N/m and lateral spring constants is below 1.1 mN/m. The equivalent reaction stiffness of the brain tissue (E=30 kPa) is estimated to be 0.94 N/m in the axial direction; i.e. the probes 10 are more compliant than brain tissue. FIG. 7C illustrates a magnified view of needle tip 24A showing electrode 16 and tethers 36.

Figure 8A:
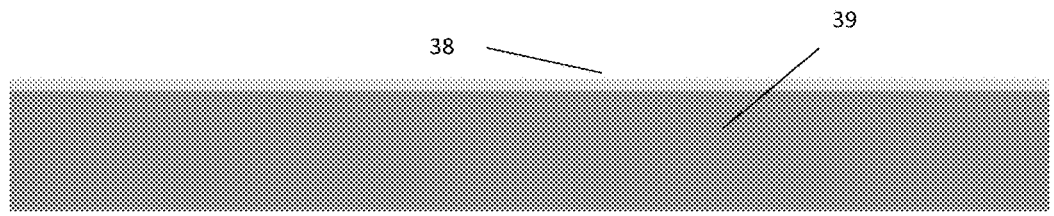
FIGS. 8A-Z show schematic cross-sections of a process flow for fabrication of the probes according to the present invention with several variations on the flow that result in separate embodiments.
Figure 8B:
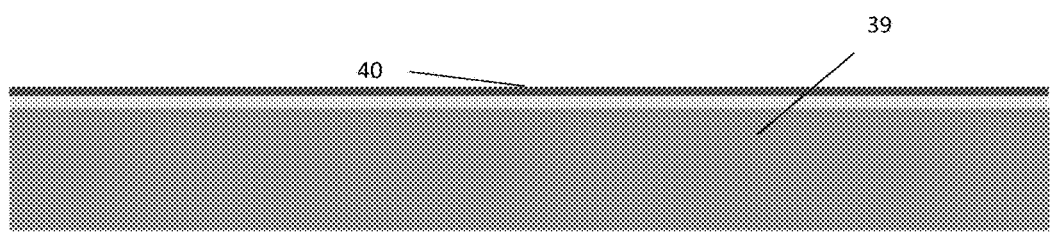
Figure 13A:
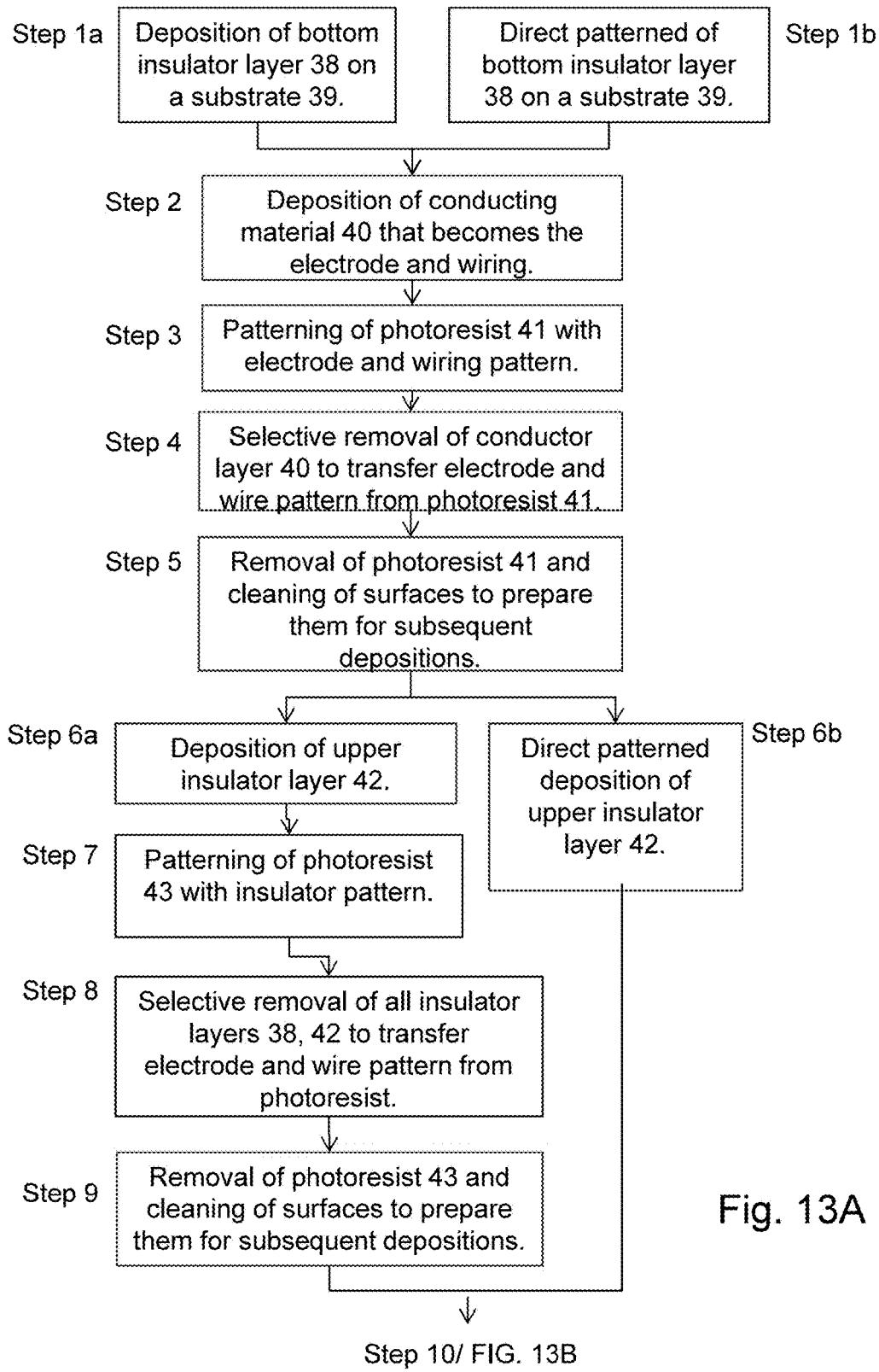
FIGS. 13A-C are process flow diagrams of an exemplary probe fabrication process of the present invention.
Figure 13B:
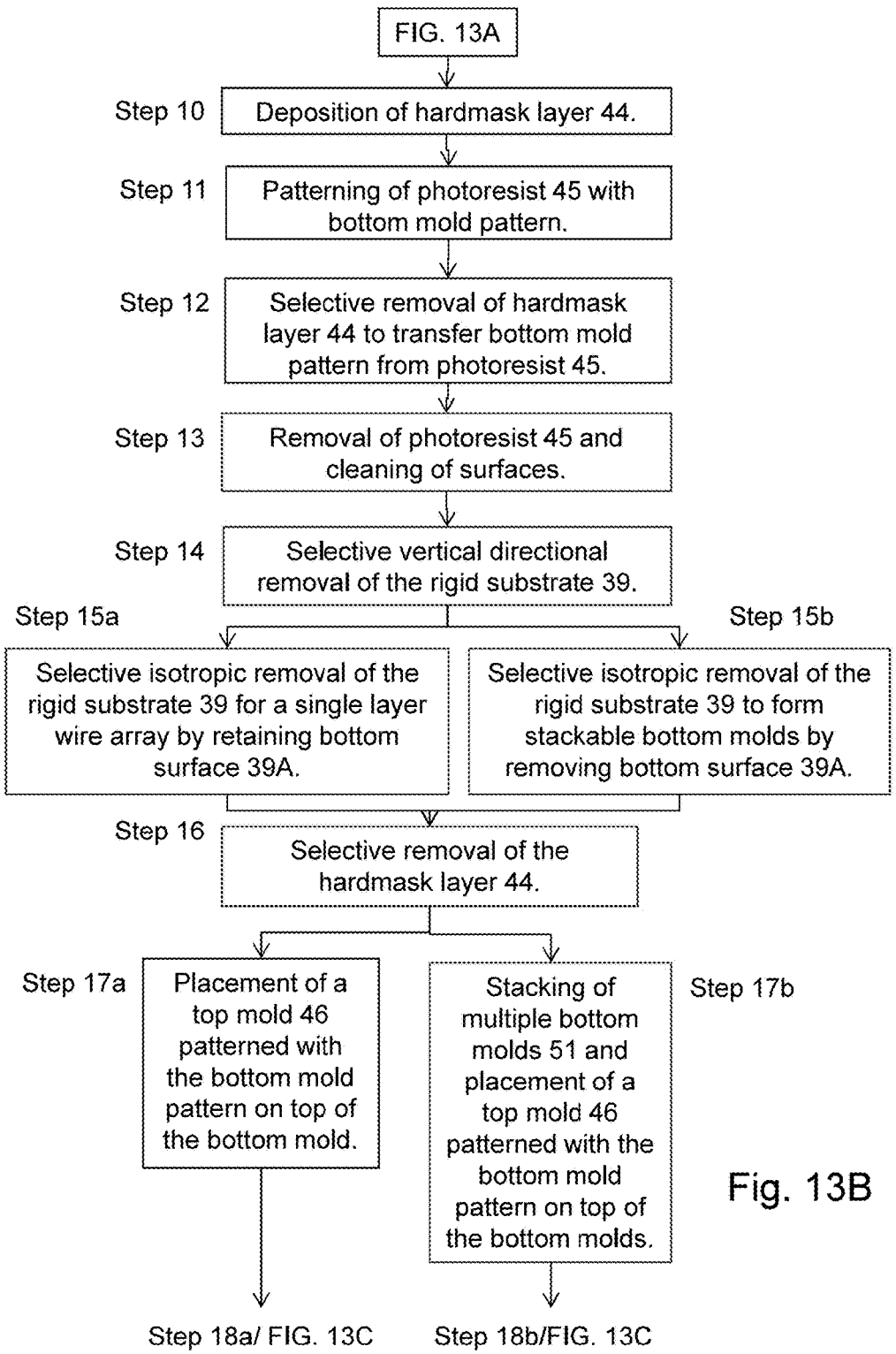
Figure 13C:
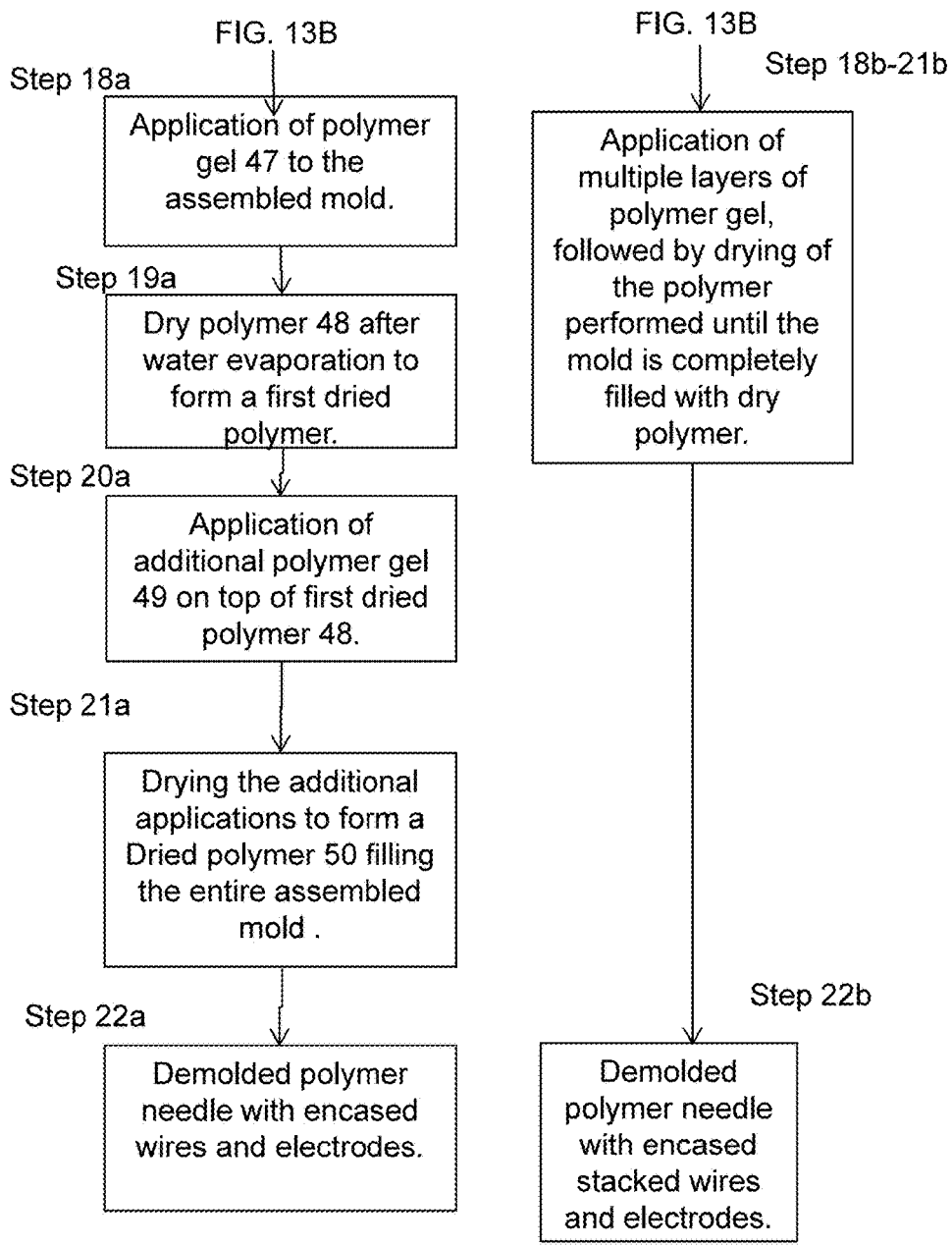

The probe wiring 14, tethers 36, tether necking regions 38 and electrodes 16 will be made using planar fabrication on silicon wafers or substrates. Embodiments of the planar process flow used in fabrication of the probes 10 according to the present invention are shown in FIGS. 8A-8Z and is described in flow chart form in FIGS. 13A-C. FIG. 8A illustrates the lower layer of insulation 38 is deposited on a substrate 39 that enables handling and manipulation during fabrication. The insulation 38 can be deposited in blanket form and patterned photolithographically, or it can be directly deposited in a pattern using techniques like 3D printing. In one embodiment, the insulation 38 is parylene-C, but could be replaced by other organic and inorganic insulating materials, like PDMS or alumina, respectively. Adhesion of parylene to the substrate may be enhanced by XeF$_2$ etch roughening of the substrate prior to deposition. The minimum thickness of the insulation 38 depends on the quality of the deposited film, and the film type, but could be as thin 100 nm. The maximum thickness is determined by the size of the cells of the tissue into which the device is being implanted. For neural tissue, where cells are on the order of 20 µm, the limit on thickness for this insulation layer 38 is 10 µm. FIG. 8B illustrates the conducting material 40 that will be patterned to form the electrode 16 and its wire interconnect is deposited on top of the insulator 38. In one embodiment, the conducting material layer 40 is Pt with a thickness of 500 nm. Platinum can be deposited directly onto polyimide with O$_2$ plasma roughening. This same procedure may be useful for direct adhesion to parylene. The lower limit on thickness of conducting material 40 depends on the resistivity of the material and its film quality, while the upper limit on its thickness is dependent on the thickness of the insulation layers 38, 42 (see FIG. 8E) because the overall thickness must be less than the size of the cells of the tissue into which the probe 10 is being implanted. It is possible for the film to range in thickness from 100 nm to 19 µm, depending on the thickness of the insulation 38.

Figure 8C:
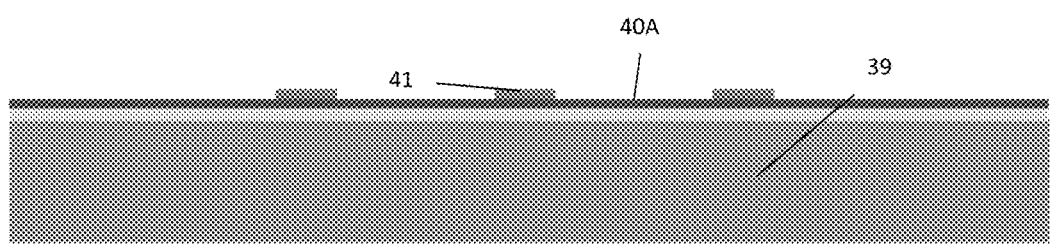
Figure 8D:
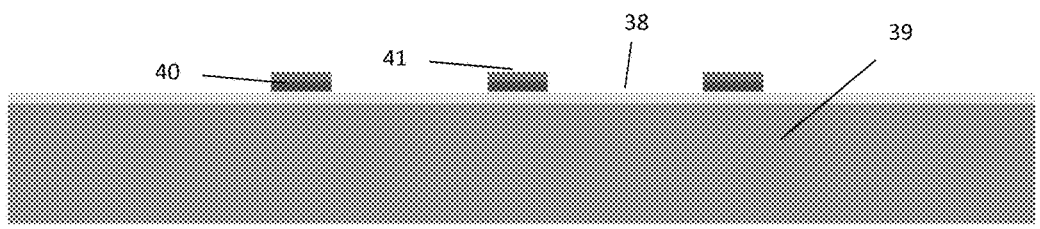
Figure 8E:
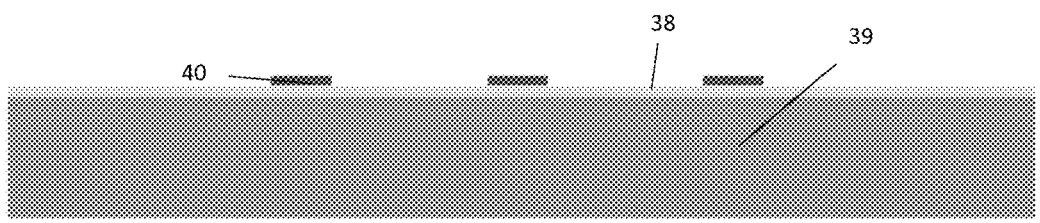
Figure 8F:
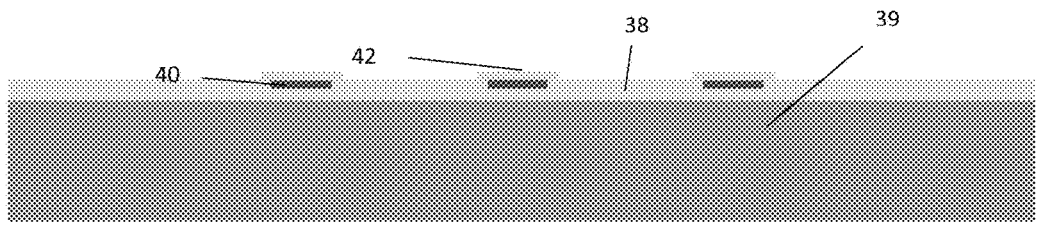

FIG. 8C illustrates that the layout pattern of the wire 14 and the electrode 16 are photolithographically printed in photoresist 41 on the outer surface 40A of the conducting material 40. The patterned photoresist 41 is used as a mask to prevent removal of the conducting material 40 under the photoresist 41 during a selective conducting material 40 removal process shown in FIG. 8D. The photoresist 41 thickness in all cases, is dependent on the thickness of the metal used for the conducting material 40 and the size of the feature to be patterned; however, the typical thickness ranges from 200 nm to 20 µm. The removal process can be performed using wet chemicals, or plasmas, depending on the conducting material 40. Following the selective conducting material 40 removal process, the photoresist 41 is removed from the surface of the substrate 39 and the substrate 39 is cleaned in preparation for subsequent depositions as shown in FIG. 8E. After cleaning, a second insulator layer 42 is deposited over the first insulator layer 38 and the patterned conductor 40 as shown in FIG. 8F. The thickness of this layer must not exceed the value that would make the total structure thickness exceed the cellular dimensions. The minimum layer thickness depends on the material choice and the minimum thickness required to ensure electrical insulation.

Figure 8G:
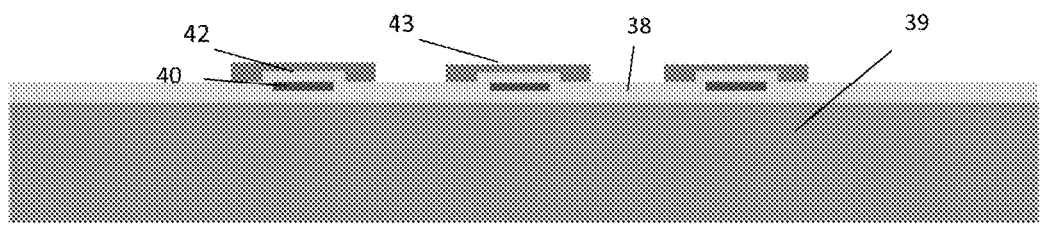
Figure 8H:
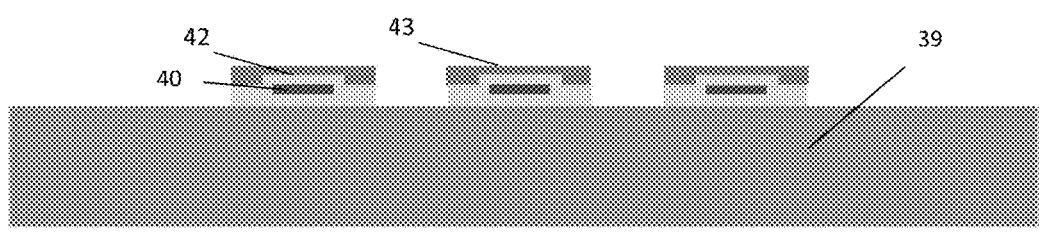
Figure 8I:
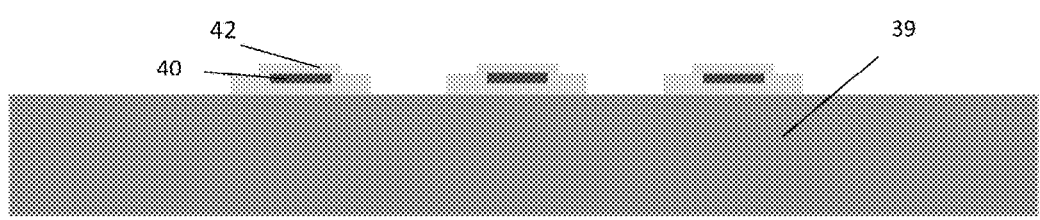
Figure 8J:
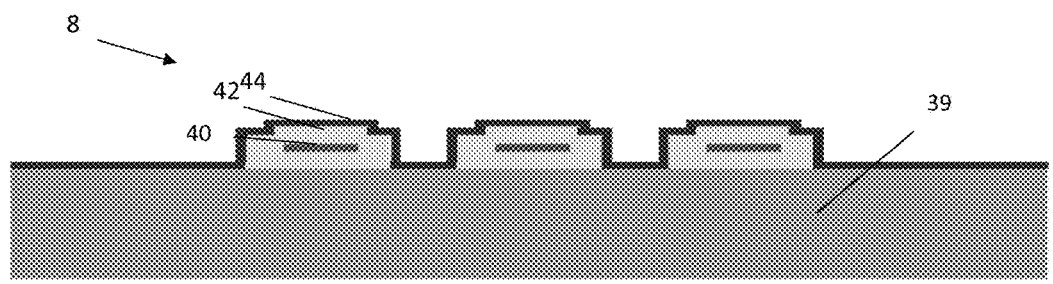
Figure 8K:
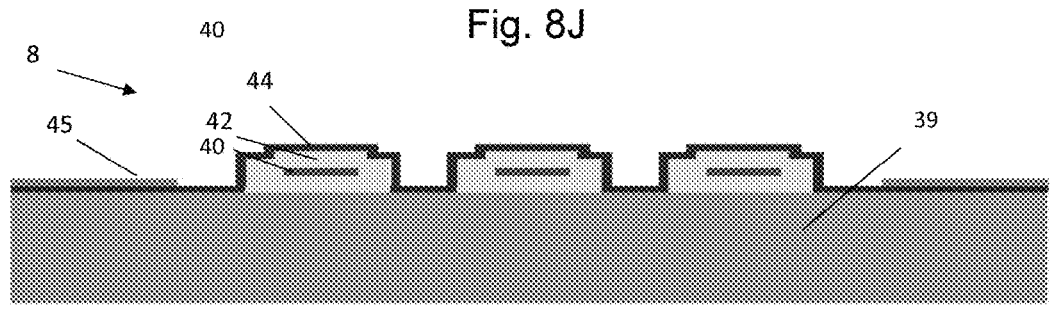
Figure 8L:
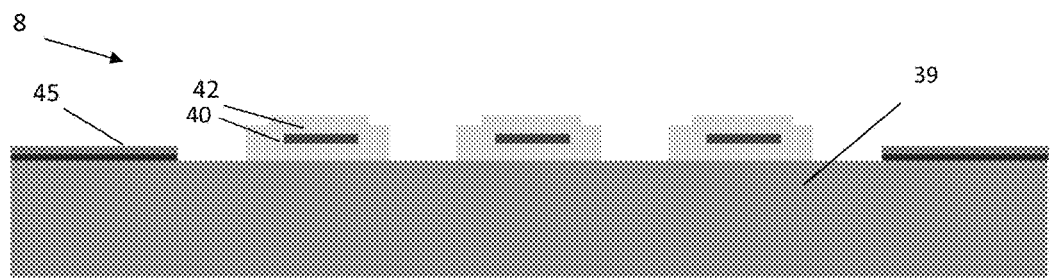
Figure 8M:
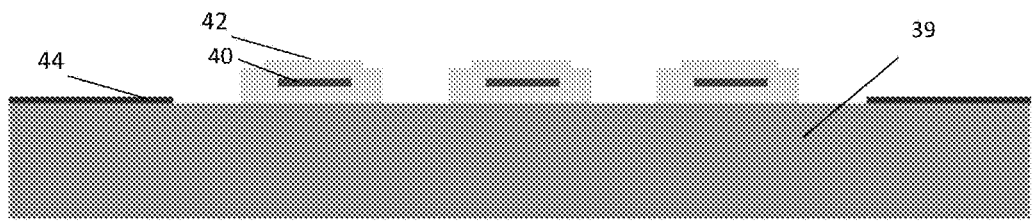
Figure 8N:
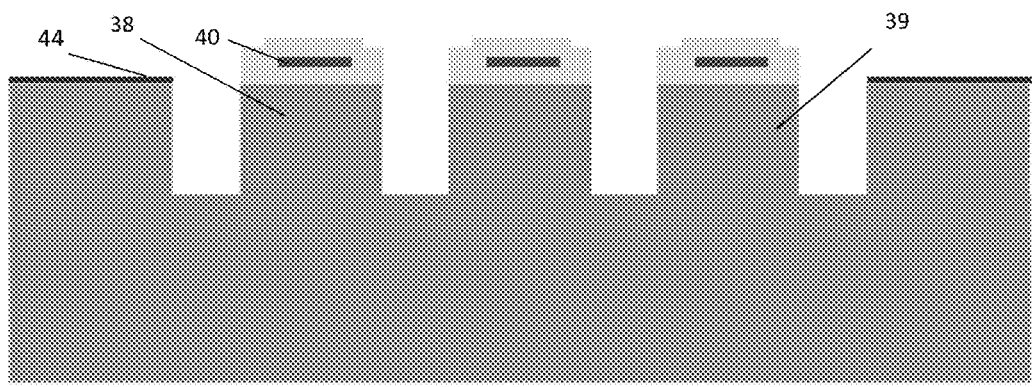
Figure 8O:
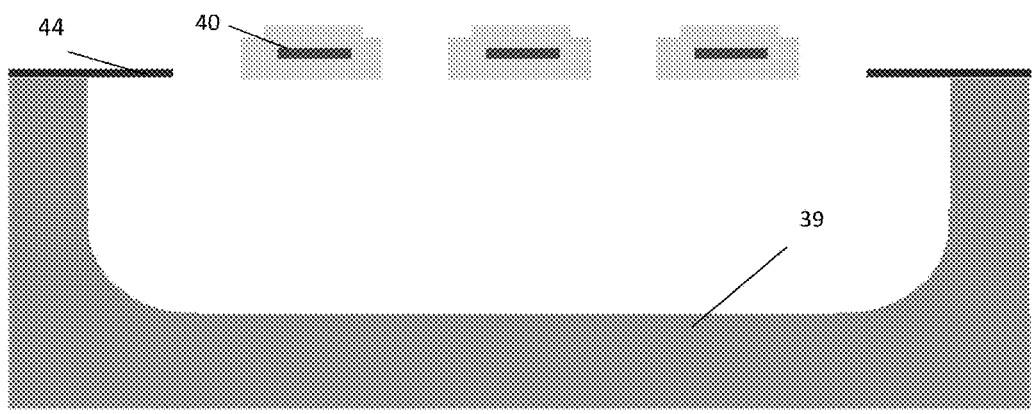

FIG. 8G illustrates that the insulated wire pattern is photolithographically formed in photoresist 43 on the surface of the upper insulator layer 42. A selective insulator layers 38, 42 removal process shown in FIG. 8H is applied to transfer the insulator pattern into the insulator layers 38, 42. Following the transfer process, the photoresist 43 is removed and the surfaces are cleaned as shown in FIG. 8I. FIG. 8J illustrates a hard mask material 44 is deposited on the top surface of the substrate 39, and the patterned insulator layers with embedded conductor. The material is called hard because of its increased resistance to processes that selectively remove the substrate material and its inorganic composition. Typical hardmask materials are metals, like Al and Cr. The minimum hardmask thickness is determined by the depth of substrate 39 that must be removed and the selectivity of the removal process to the hardmask materials. The minimum thickness of hardmask 44 is typically selected and this is around 100 nm for Al. FIG. 8K illustrates patterning of photoresist 45 with bottom mold pattern on the hardmask 44. FIG. 8L illustrates selective removal of hardmask layer 44 to transfer bottom mold pattern from photoresist 43. FIG. 8M illustrates removal of photoresist 45 and cleaning of surfaces. In one embodiment of the invention the substrate 39 is Si and is selectively removed using a process called Deep Reactive Ion Etch (DRIE) which etches Si only in a vertical direction as shown in FIG. 8N. The depth of the DRIE Si etch is driven by the desired dimensions of the encasement. In one embodiment, the depth of this part of the process is about 40 µm. Following DRIE, columns of substrate 38 remain under the insulated wire pattern and electrodes 40. In FIG. 8O illustrates the wire pattern and electrodes 40 being suspended when these regions of substrate 38 are removed using a process that removes material in all directions at the same rate. This isotropic process is performed until there is no Si left under the wires and electrodes 40 and is performed for a length of time dependent on the rate at which Si etches and the width of the wires and electrodes. The depth of the bottom mold is dependent on the desired thickness of the final encasement. In one embodiment the depth of the bottom mold is 60 µm, but could range from 5 µm to 100 µm depending on the desired needle thickness and the desired position of the wire and electrode within the needle. In one embodiment of the present invention, both the top and bottom of the platinum are clad in Ti or TiN to ensure adhesion on both sides. In this case, the platinum electrode would conveniently become exposed during the Si DRIE step illustrated in FIG. 8I, which will also directionally etch Ti. An overlap of parylene around the exposed electrode will be designed to help "lock in" the electrode 16 and prevent stress-induced etching of the metal-parylene interface. Following electrode formation, its recording and stimulating properties can be enhanced by applying materials such as PEDOT (Poly(3,4-ethylenedioxythiophene)) that reduce the electrical impedance to neural signals. The deposition of materials that modify the electrode surface can be done in several ways, for example, electrochemically or by direct additive deposition using technologies like dip pen nanolithography.

The silicon deep reactive-ion etch (DRIE) and isotropic etch steps are subject to ARDE effects that can be used to create three-dimensional structure in the needle mold. These effects, along with the layout pattern of meandering wires, tethers, tether necking regions and the outline of the needle, define the lower half of the needle shape. In the regions covered by the layout pattern the substrate is not removed until the final etching process shown in FIG. 8N and this results in a shallow 3D structure on the bottom surface of the bottom mold that corresponds to the meandering wires, tethers, and tether necking regions.

Figure 8P:
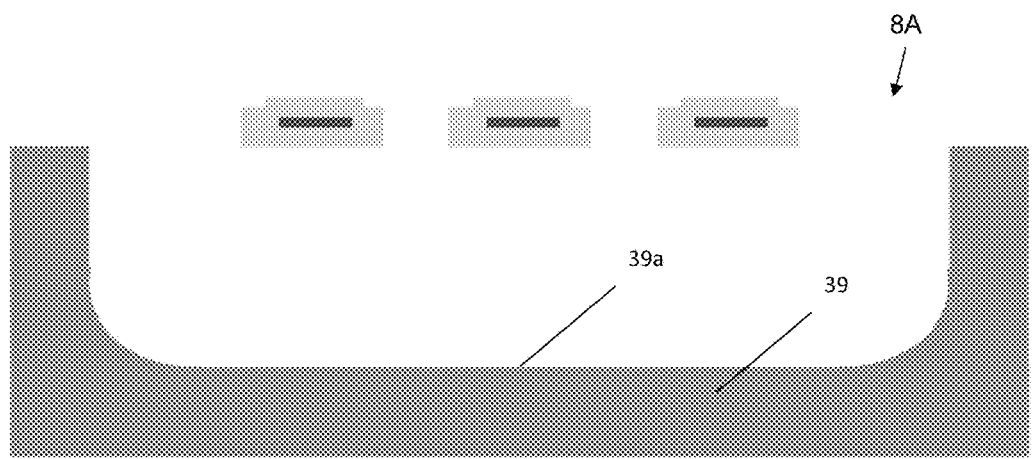
Figure 16A:
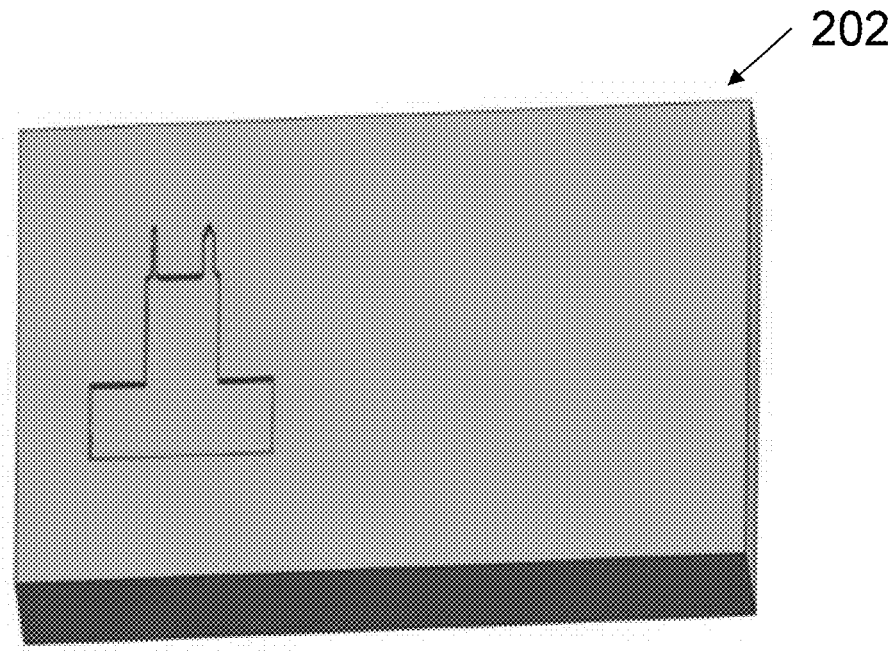
FIGS. 16A-H are pictorial illustrations of the top mold fabrication method of the present invention.
Figure 16B:
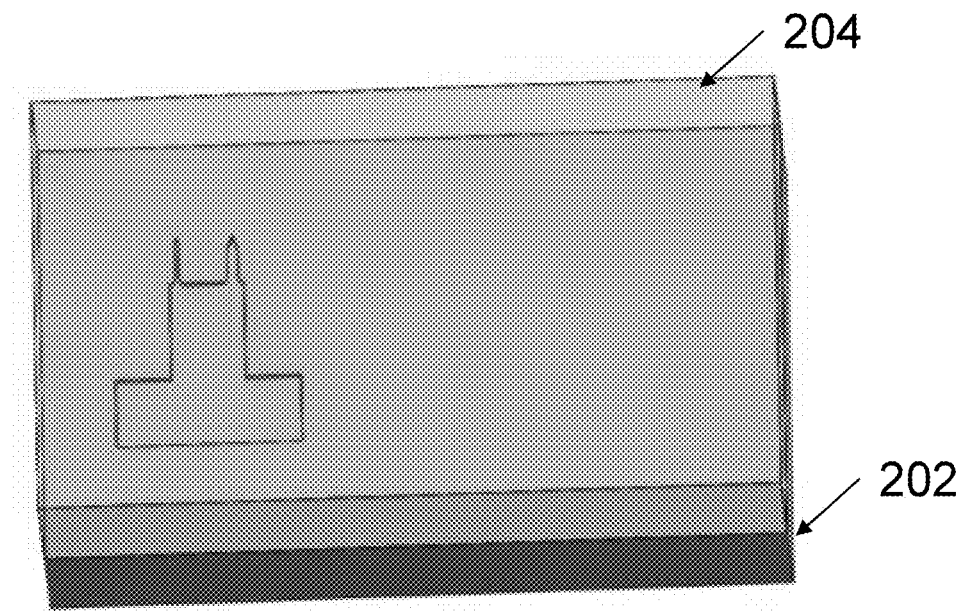
Figure 16C:
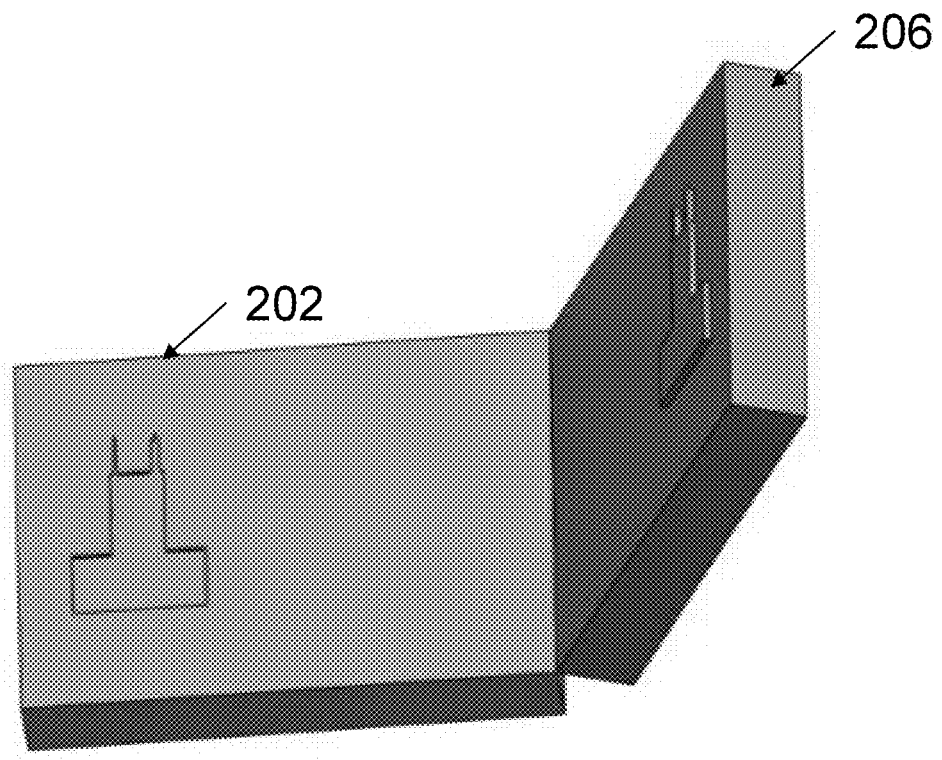
Figure 16D:
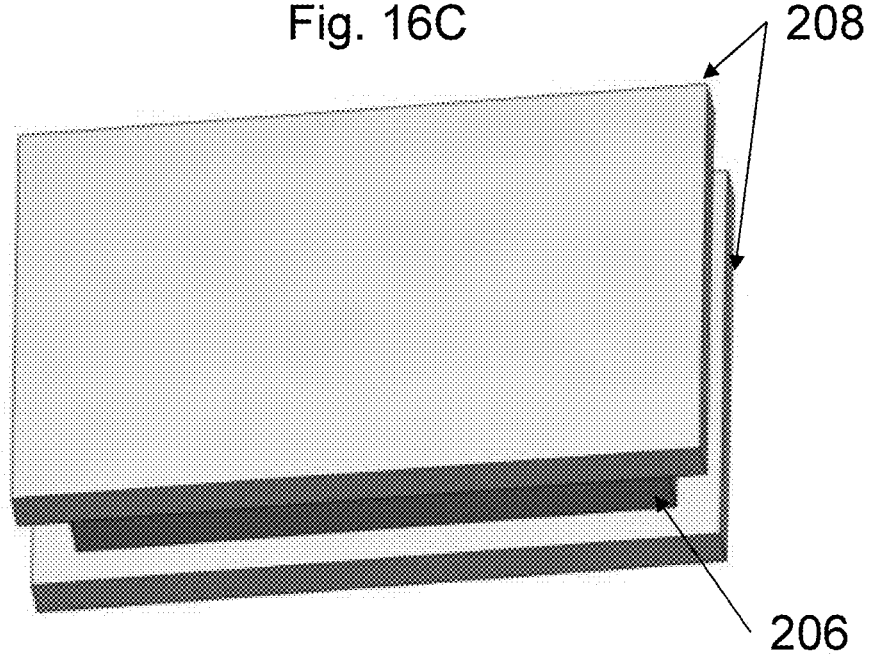
Figure 16E:
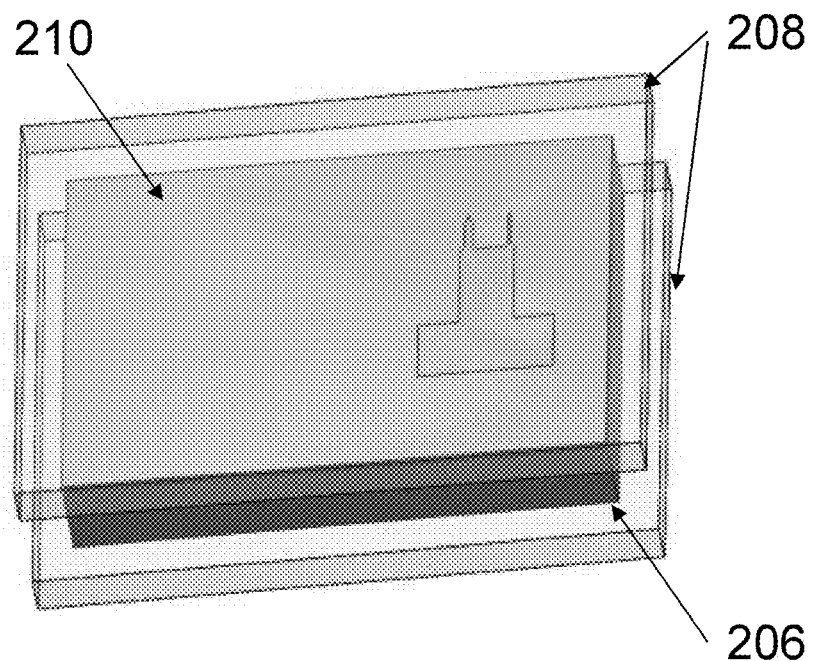
Figure 16F:
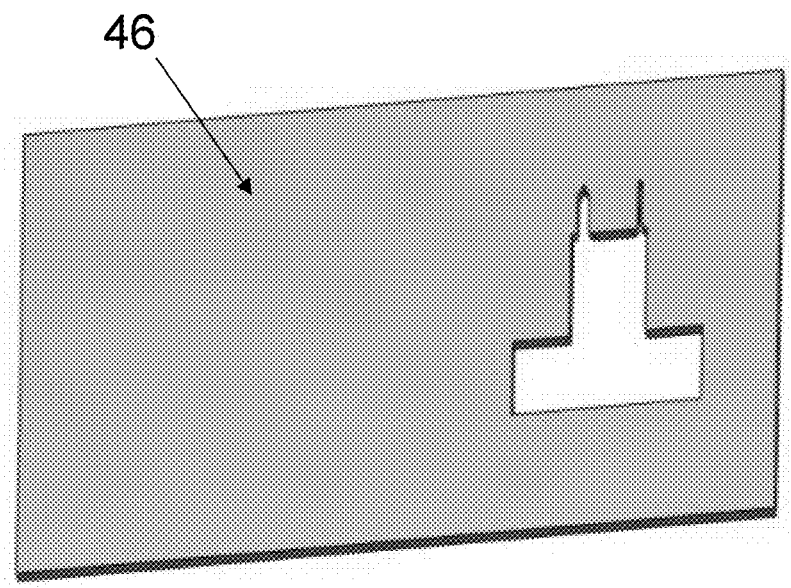
Figure 16G:
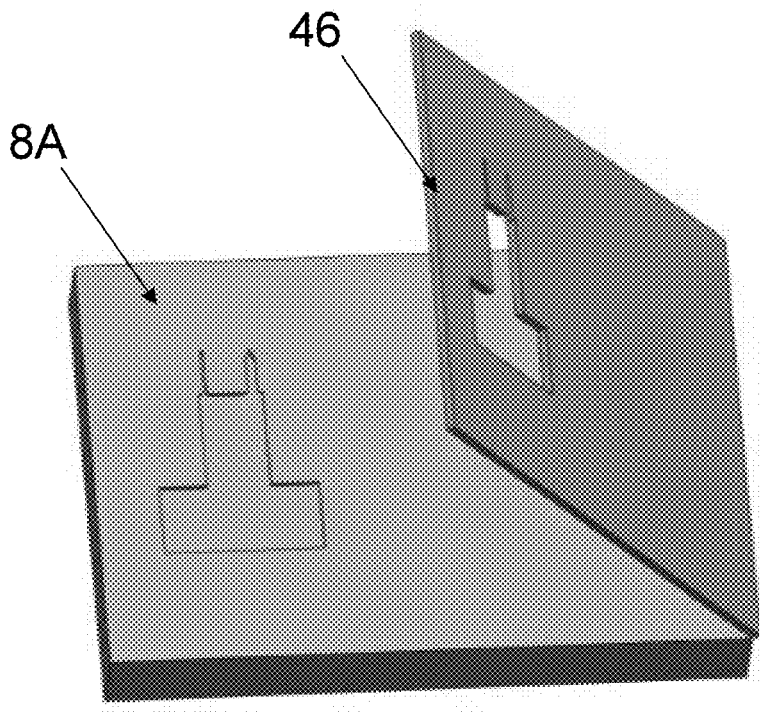
Figure 16H:
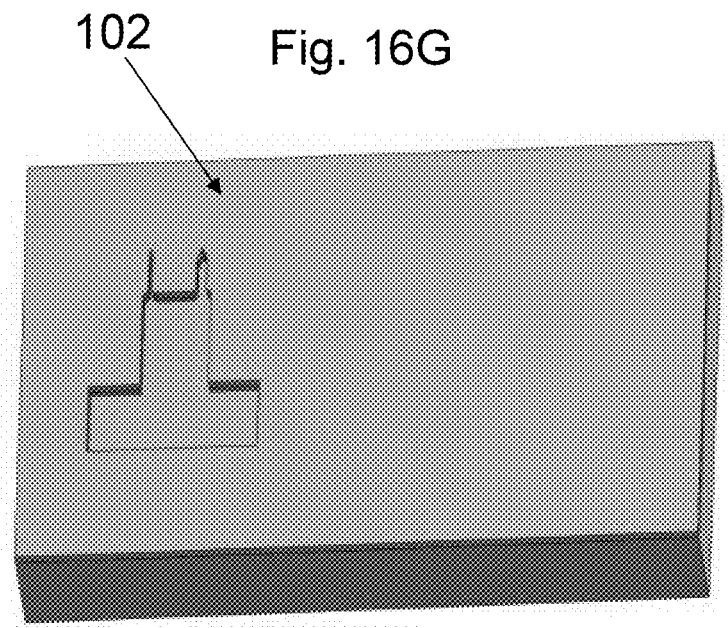
Figure 17:
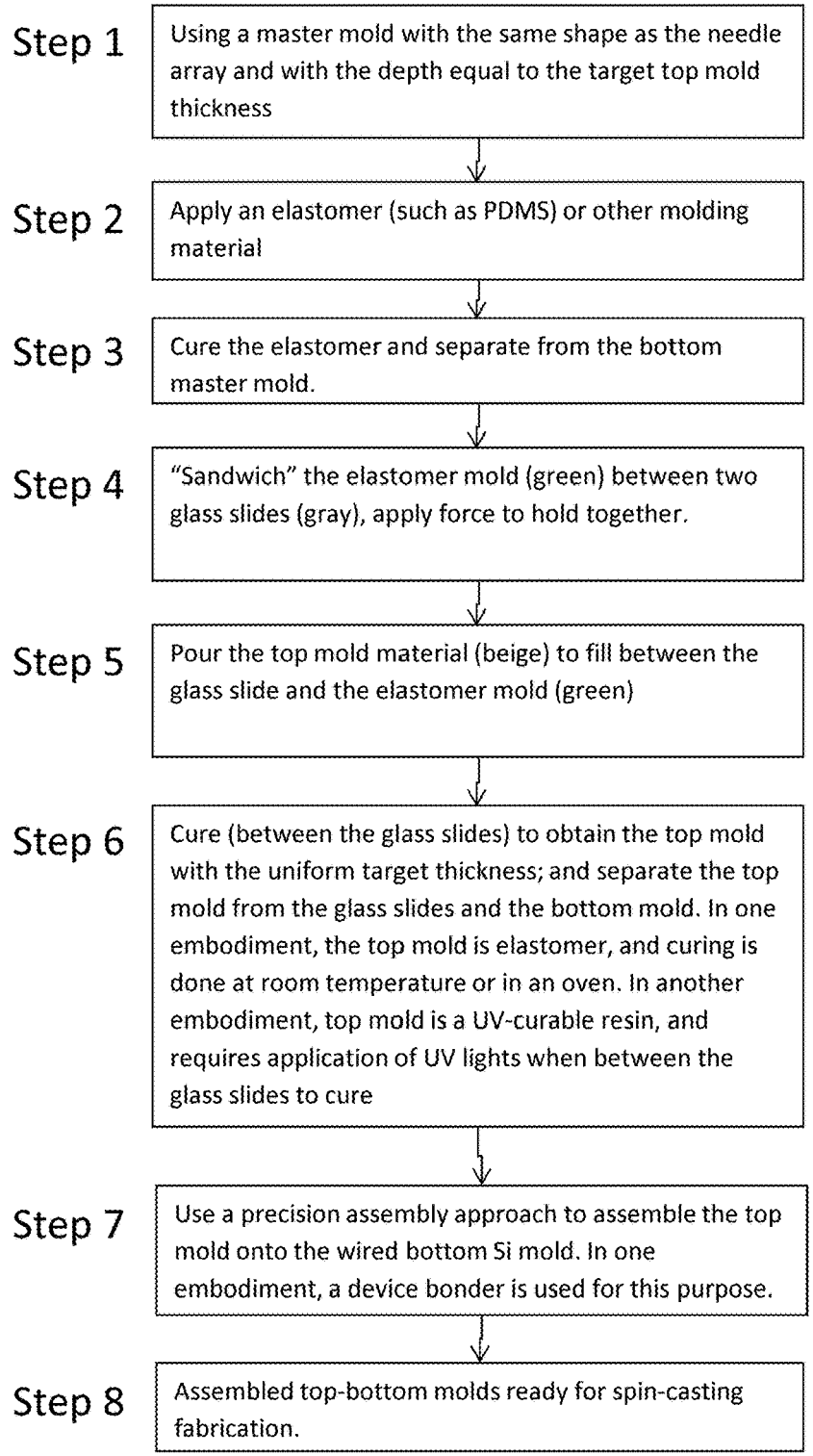
FIG. 17 is a process flow diagram of an exemplary top mold fabrication method and top/bottom mold assembly in the present invention.

The upper needle shape is set by a top mold 46 (see FIG. 8Q) with a shape defined by the outline of the needle, made from an elastomer, such as PDMS or PVS, a resin, such as UV-curable resins, or any other polymer or dissolvable materials. The top mold fabrication is described in FIGS. 16A-H and 17 and uses a technique referred to as the sandwich method. In Step 1 (FIG. 16A), a master mold that includes the needle shape is used. The master mold can be formed in several ways, for example from a PMMA master mold 202 made by mechanical micromilling or from a Si master mold made by patterning a Si substrate with the needle pattern and applying the process steps of Si Deep reactive-ion etching (DRIE) (FIG. 8N), Si isotropic etching (FIG. 8O), and wet strip aluminum mask 44 (FIG. 8P). The depth of the needle-shaped mold area is made to be the same as the target top-mold thickness. In Step 2 (FIG. 16B), an intermediate mold material 204, such as PDMS, is applied onto the master mold 202. In Step 3 (FIG. 16C), the intermediate mold material 204 is cured and separated from the master mold 202 to form intermediate mold 206. In Step 4 (FIG. 16D), the intermediate mold 206 is sandwiched between two glass slides 208, and appropriate force is used to hold the three pieces together. In Step 5 (FIG. 16E), the top mold material 210 is poured between the top glass slide 208 and the intermediate mold 206. In one embodiment, top mold material 210 is an elastomer such as PVS. In another embodiment, the top mold material 210 is a UV-curable resin. In Step 6 (FIG. 16F), the top mold material 210 is cured to form the top mold 46. For example, if UV-curable resin is used, UV rays are emitted from a UV-lamb is used to cure the top mold material 210. The top mold 46 is then separated from the glass slides 208 and the intermediate mold 206. In Step 7 (FIG. 16G), a precision assembly approach is used to assemble the top mold 46 onto the wired Si bottom mold 8A. In one embodiment, a device bonder is used for this assembly. Thus, in Step 8 (FIG. 16H) the assembled top-bottom mold 102 with wires is obtained, which will be subsequently used for spin-casting.

Figure 8Q:
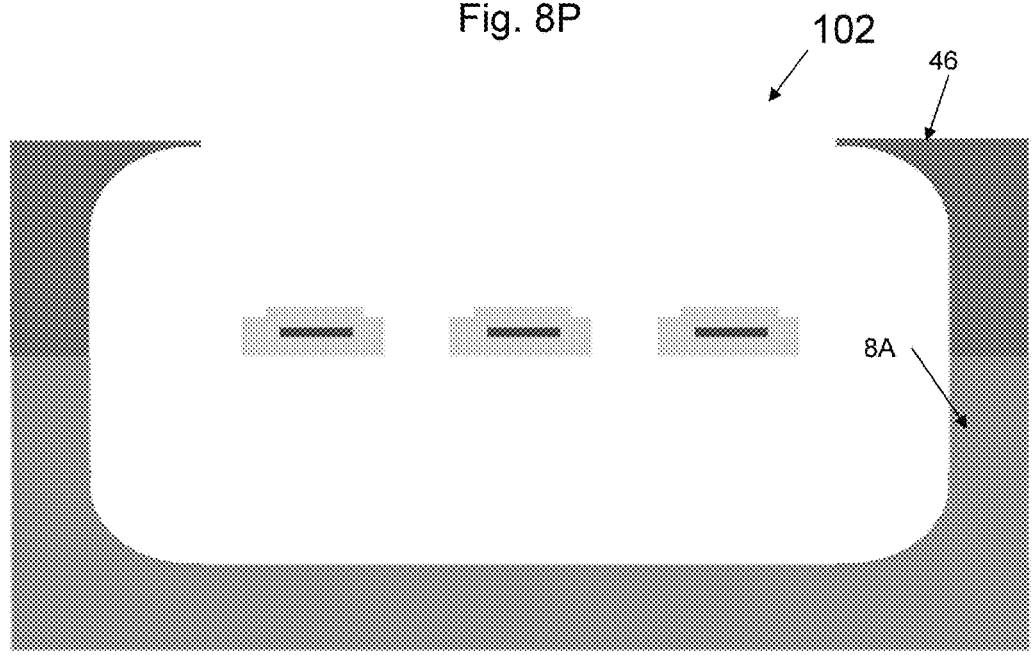

Following completion of the bottom mold 8A, a top mold 46 is applied in one embodiment to form assembled mold 102 as shown in FIG. 8Q. In another embodiment, shown in FIG. 8W, the substrate is etched through so the bottom mold 51 is completely open. Several bottom molds 51 are stacked together as shown in FIG. 8X and the top mold 46 is applied to form a structure in which wires and electrodes are arrayed in a 3-dimensional matrix. FIG. 8Y is an illustration of the molds 46, 51 filled with a hydro-gel of CMC or other dissolvable substance by a process discussed in detail below to form probe 10 in FIG. 8Z.

Figure 8R:
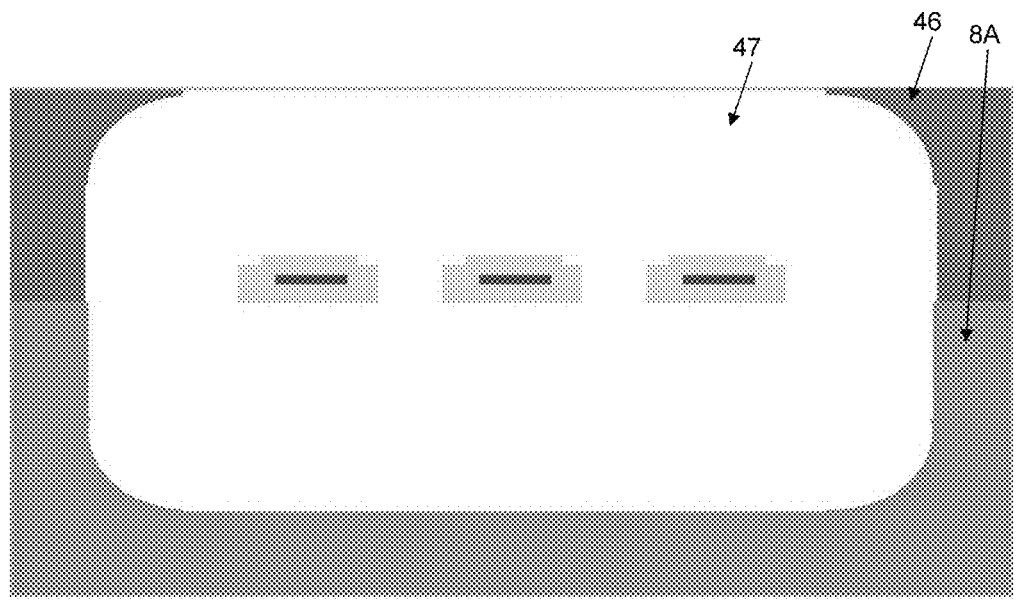
Figure 8S:
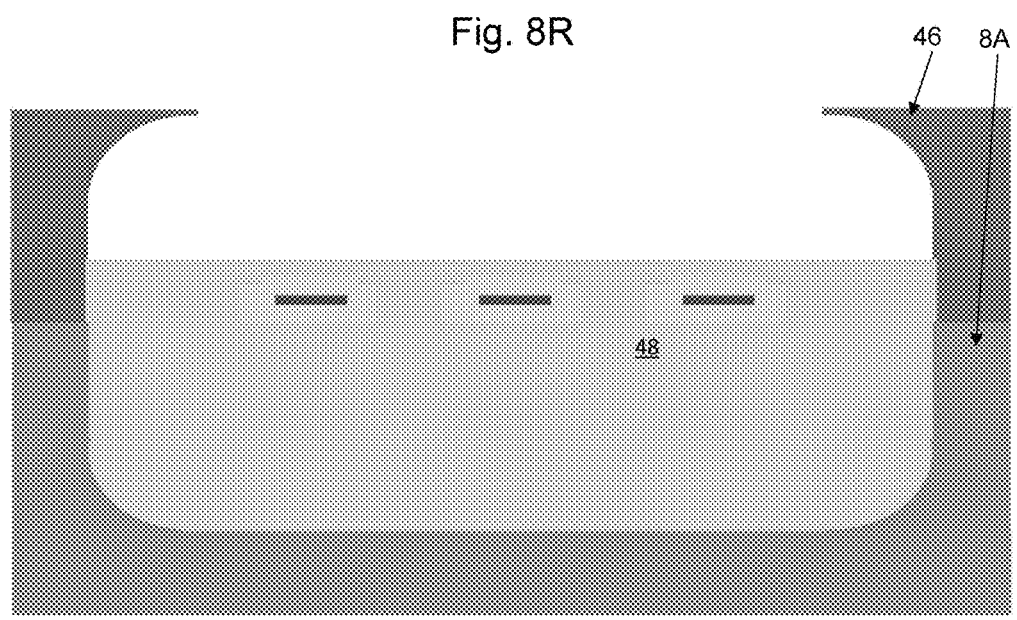
Figure 8T:
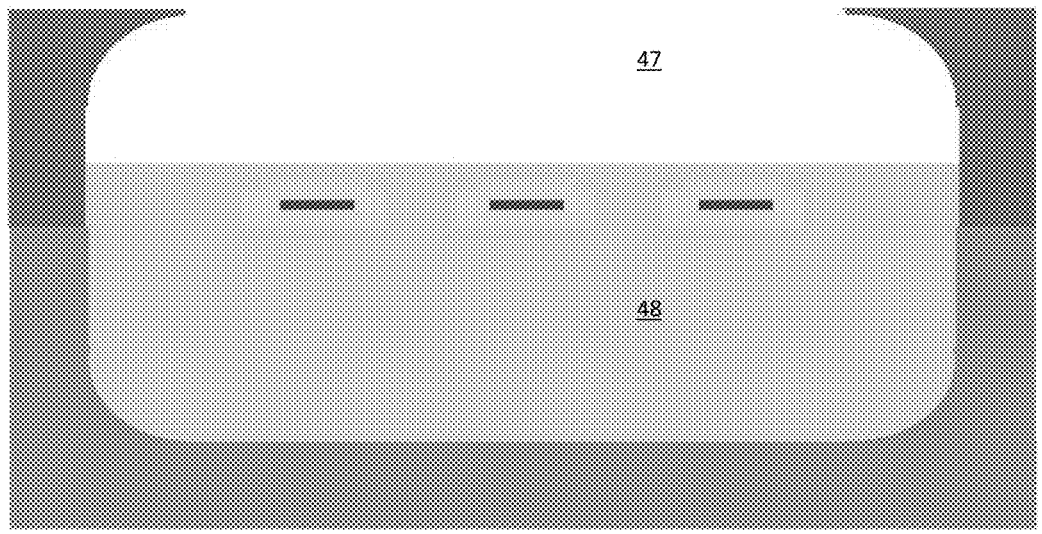
Figure 8U:
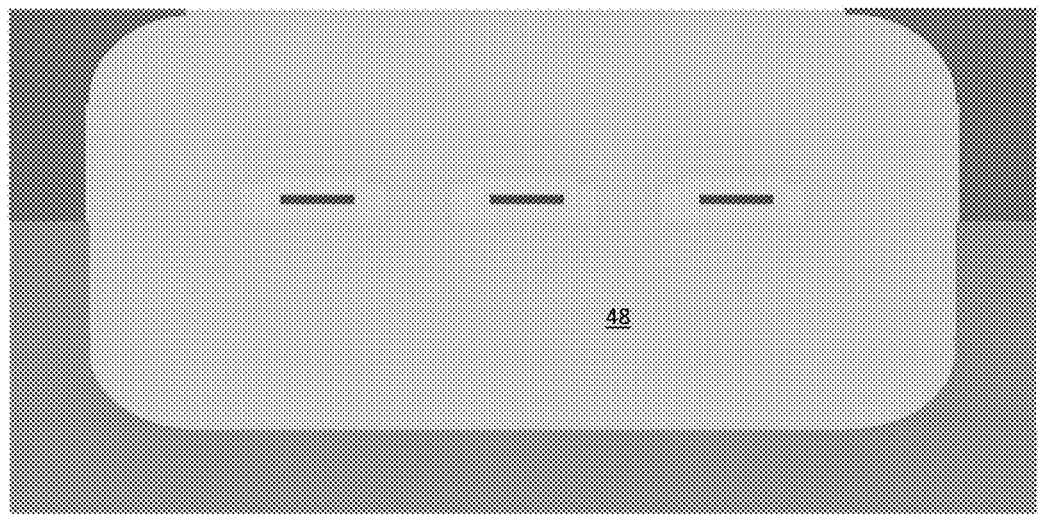
Figure 8V:
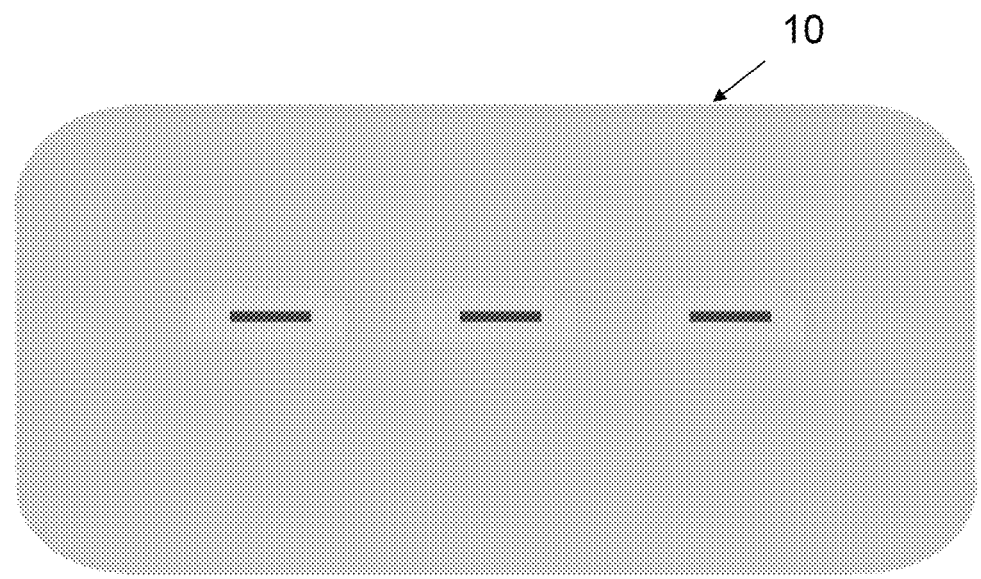
Figure 8W:
Figure 8X:
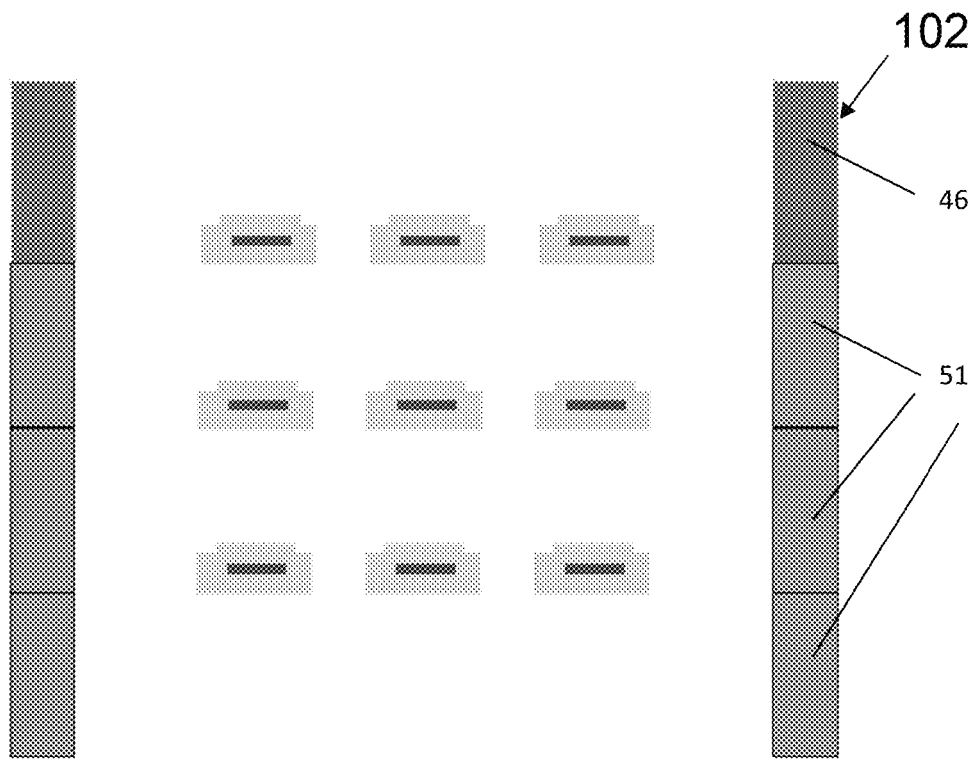
Figure 8Y:
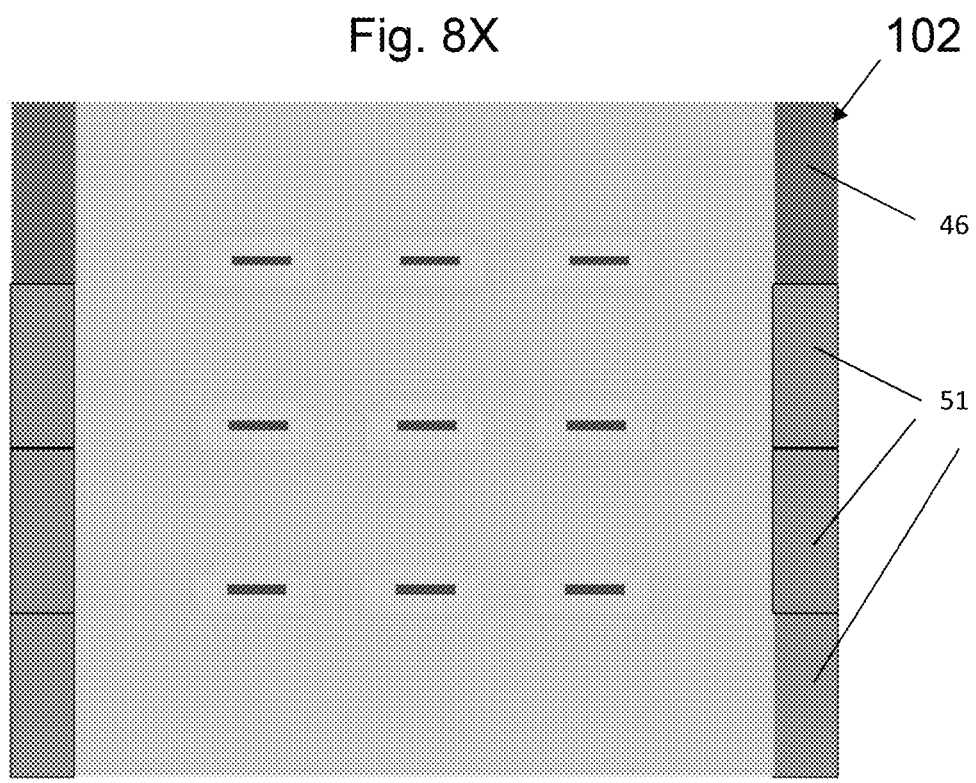
Figure 8Z:
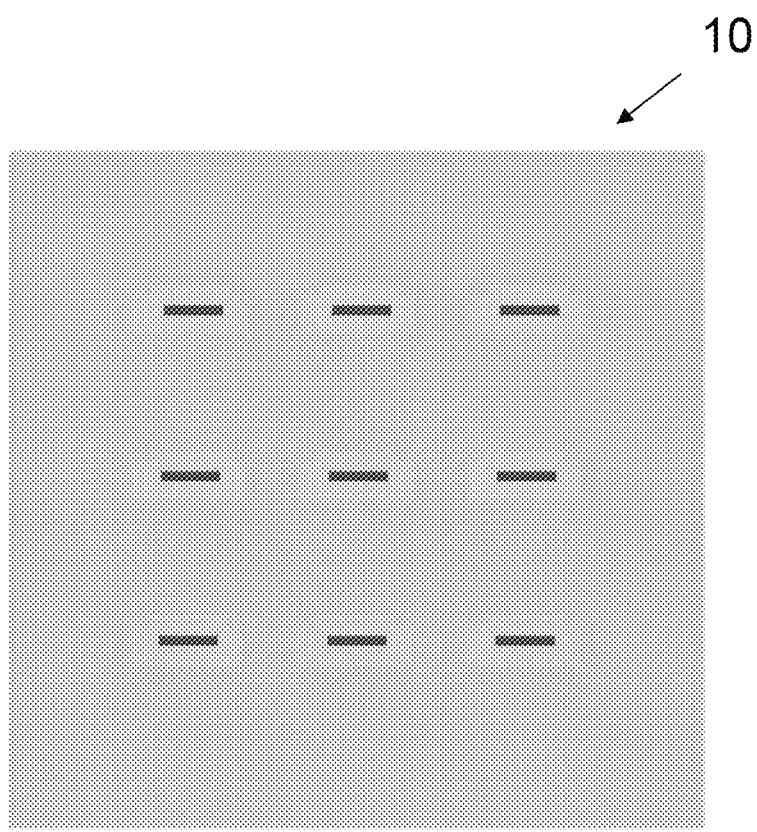
Figure 14A:
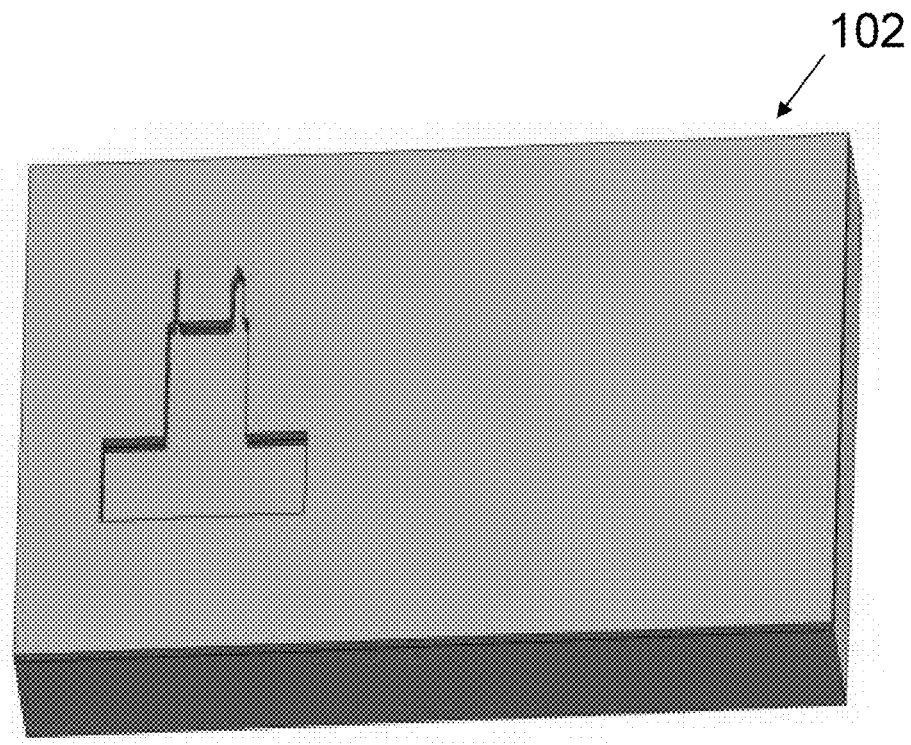
FIGS. 14A-H are pictorial illustrations of the spin casting method to fabricate the needle of the probe of the present invention.
Figure 14B:
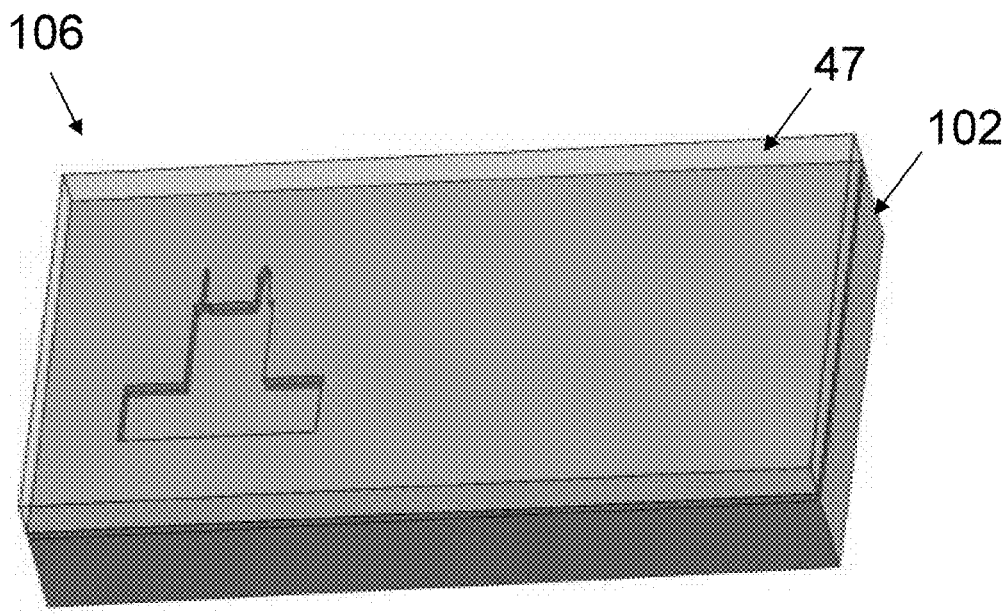
Figure 14C:
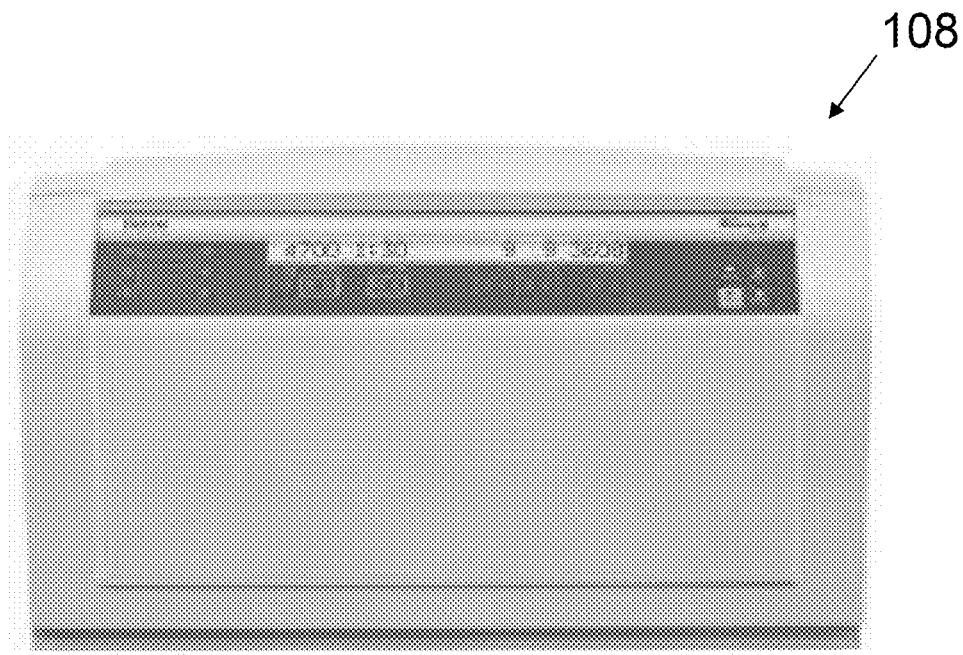
Figure 14D:
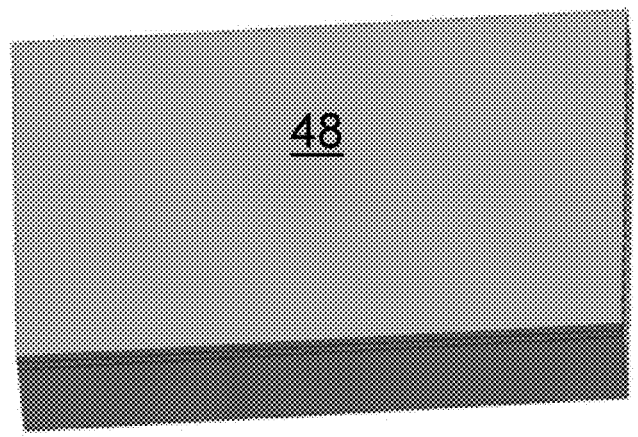
Figure 14E:
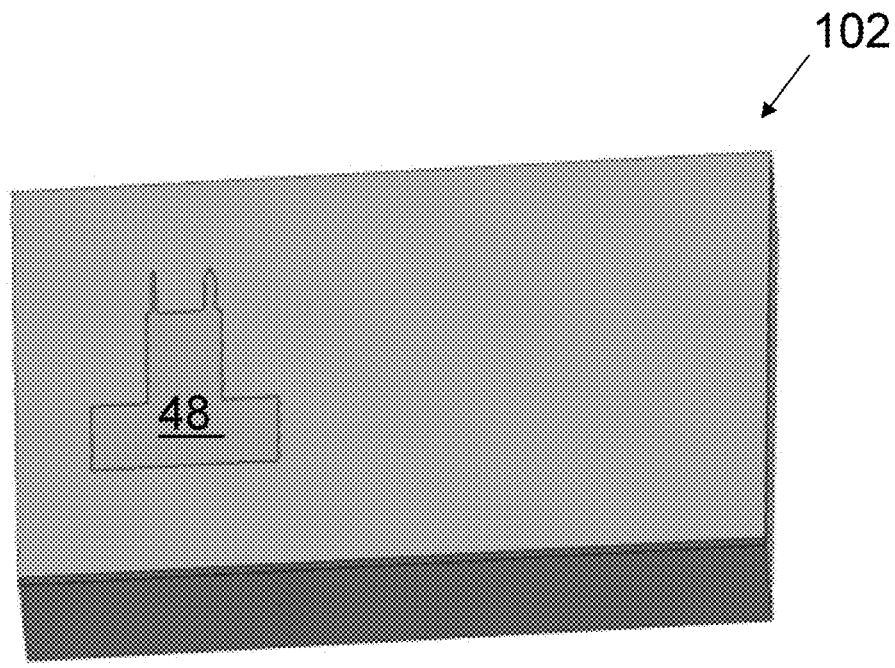
Figure 14F:
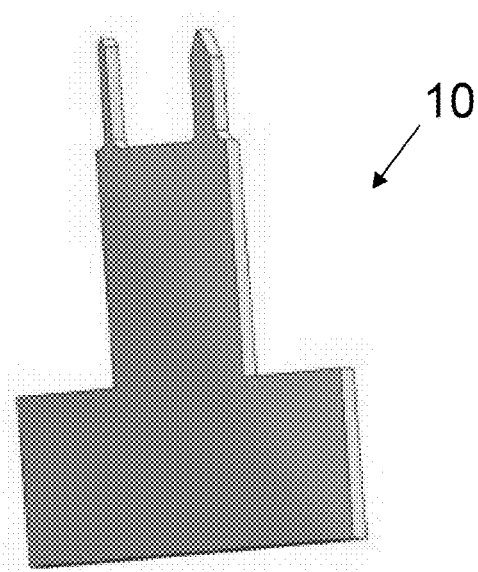
Figure 14G:
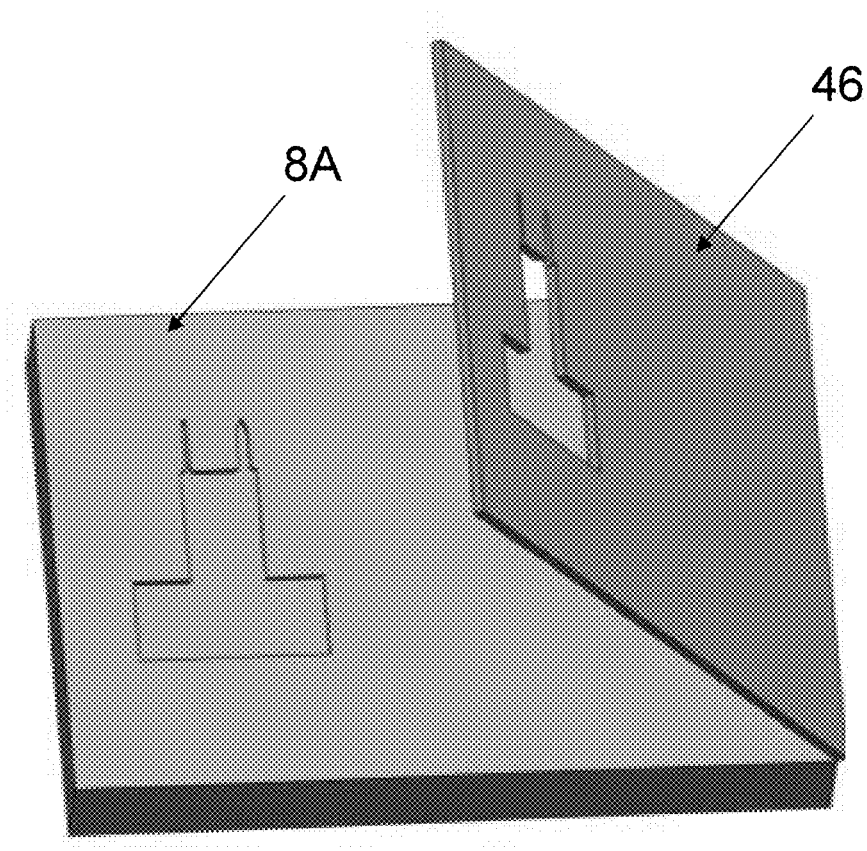
Figure 14H:
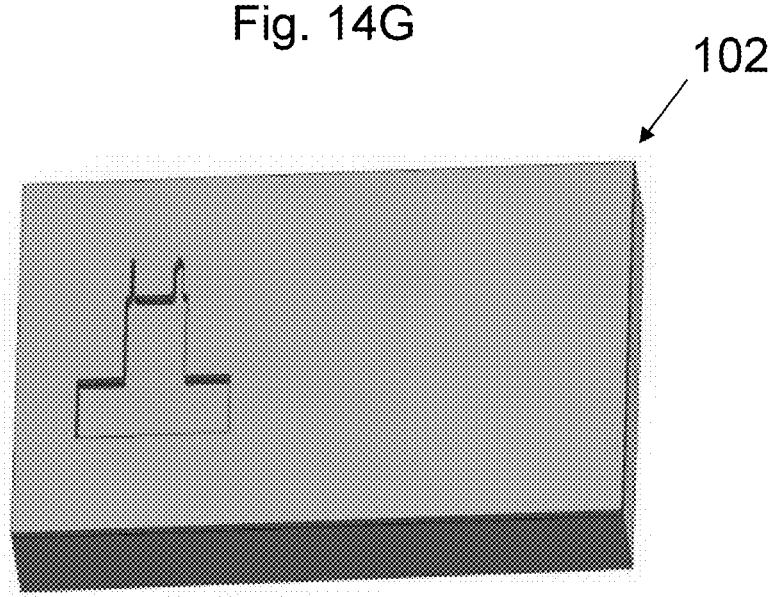
Figure 15:
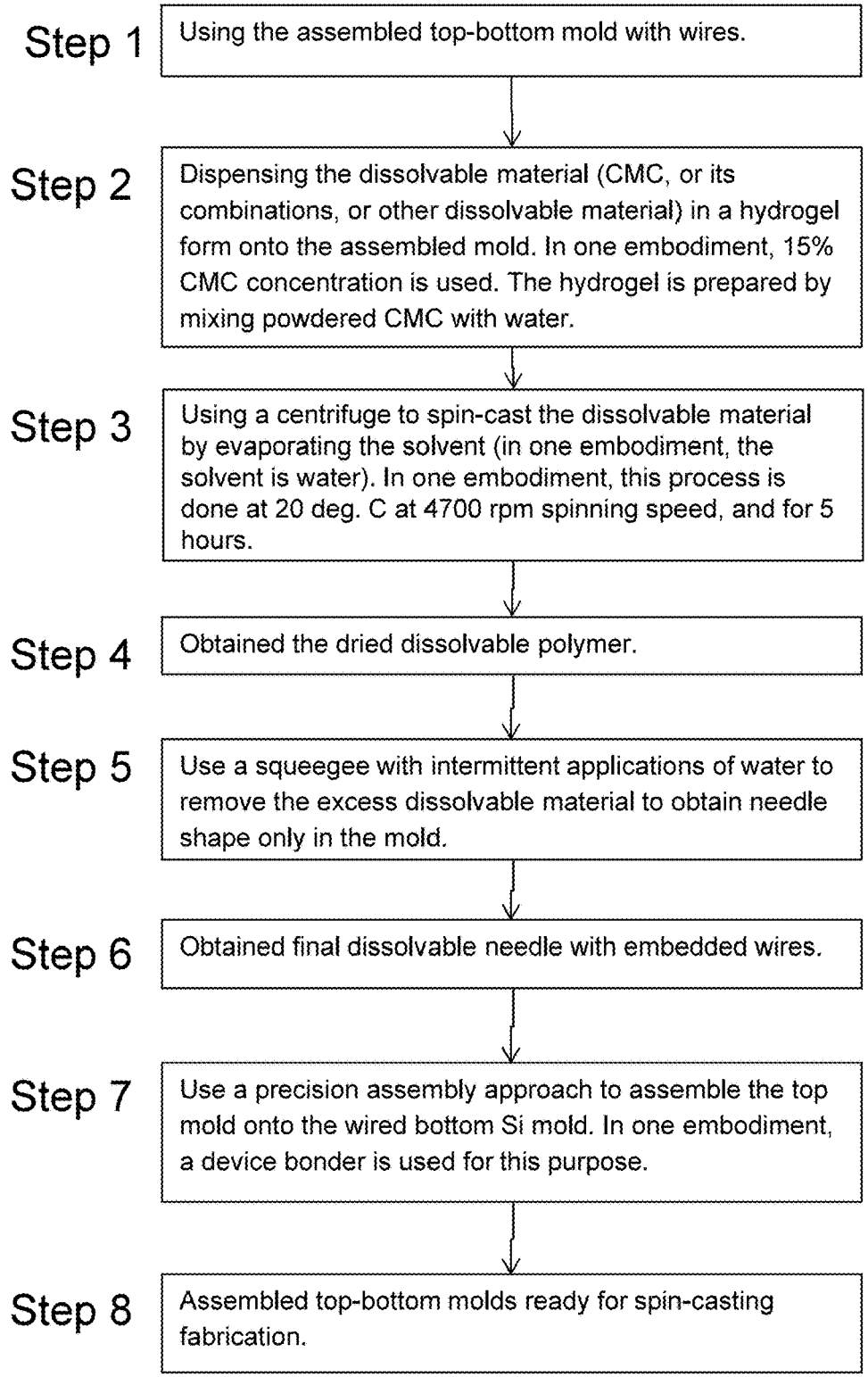
FIG. 15 is a process flow diagram of an exemplary fabrication process of the needle in the present invention.

The hydro-gel of CMC 47 is poured into the PDMS-Si mold (FIG. 8R). A more detailed description of the spin-casting process is included in FIGS. 14A-H and 15. In Step 1 (FIG. 14A), the assembled mold 102 obtained from the sandwich molding is used. In Step 2 (FIG. 14B), a hydrogel 47 of the dissolvable (needle) material is applied on the assembled mold 102 to form hydrogel-dispensed assembled molds 106. In one embodiment, the dissolvable material is CMC, and the hydrogel 47 has 15% concentration of CMC and the rest is water. Other solvents can be used in the process based on the choice of dissolvable polymer. In Step 3 (FIG. 14C), a high-g laboratory centrifuge 108 is used to spin the hydrogel-dispensed assembled molds 106. The centrifuge 108 ensures removal of air pockets from the hydro-gel 47 and the complete filling of the mold 102. In one embodiment, the top of the top mold is completely exposed. In another embodiment, release holes (not shown) on top of the top mold 46 are used. Through the centrifuging, the water is evaporated in controlled low temperature, dry conditions, and the dissolvable needle material (e.g., CMC) 47 is solidified to form solidified layer 48. If needed, to ensure complete filing of the mold, considering the shrinkage of CMC, the application of additional layers of CMC 48 is repeated twice, or more times until the needle reaches the desired dry thickness (FIGS. 8S-8U). The final thickness depends on the required mechanical stiffness of the needle to ensure penetration of the tissue without breakage. In one embodiment, this thickness is 125 µm but can range from 50 µm to 200 µm for insertion into dura-resected brain when the needle length is 1.5 mm. In Step 4 (FIG. 14D), the dried CMC 48 on the assembled mold is obtained. In Step 5 (FIG. 14E), a squeegee method is used to remove the excess CMC. In this method, a wiping device such as a sharp blade with a soft coating (e.g., PDMS) is used, and a number of repeated steps of water application and squeegeeing followed until the excess material is completely removed, as shown in Step 5. Considerable shrinkage of the CMC during this process facilitates easy separation of CMC from the assembled mold 10, as seen in Step 6 (FIG. 14F). In Step 7 (FIG. 14G), a precision assembly approach is used to assemble the top mold 46 onto the wired Si bottom mold 8A. In one embodiment, a device bonder is used for this assembly. Thus, in Step 8 (FIG. 14H) the assembled top-bottom mold 102 with wires is obtained, which will be subsequently used for spin-casting. The batch fabrication allows multiple probe designs to be placed on a single mask set, or to fabricate multiple probes of the same design. FIG. 8V illustrates the final probe 10 after being removed from the molds.

Now returning to FIGS. 13A-C that illustrate in process flow diagrams of an exemplary probe fabrication process of the present invention. The process includes many options:

Step 1a or 1b: The insulator layer 38 can be formed on a substrate 39 by depositing (Step 1a) or by direct patterning (Step 1b);

Next, all above steps continue to Steps 2-5:

Step 2: Depositing of conductor 40 that becomes the electrode and wiring;

Step 3: Patterning of photoresist 41 with electrode and wiring pattern;

Step 4: Selective removal of conductor layer 40 to transfer electrode and wire pattern from photoresist 41;

Step 5: Removal of photoresist 41 and cleaning of surfaces to prepare them for subsequent depositions;

Next, after completion of all the above step the process continues to either Steps 6a-9 or Step 6b: The upper insulator layer 42 can be formed by either of the following steps:

Option 1-Steps 6a-9:

Step 6a: Deposition of upper insulator layer 42;

Step 7: Patterning of photoresist 43 with insulator pattern;

Step 8: Selective removal of all insulator layers 38 42 to transfer electrode and wire pattern from photoresist; and Step 9: Removal of photoresist 43 and cleaning of surfaces to prepare them for subsequent depositions.

Option 2:—Step 6b

Step 6b: Direct patterned deposition of upper insulator layer 42.

Next, all above steps continue to Steps 10-14:

Step 10: Deposition of hard mask layer 44;

Step 11: Patterning of photoresist 45 with bottom mold pattern;

Step 12: Selective removal of hard mask layer 44 to transfer bottom mold pattern from photoresist 43;

Step 13: Removal of photoresist 43 and cleaning of surfaces;

Step 14: Selective directional removal of the rigid substrate 39;

Next, all the above steps will continue to either Step 15a or Step 15b: removal of rigid substrate 39 can be performed by Selective isotropic removal of the rigid substrate 39 for a single layer wire array by retaining bottom surface 39A (Step 15a) or selective isotropic removal of the rigid substrate 39 to form stackable bottom molds by removing bottom surface 39A (Step 15b);

After completion of either Step 15a or Step 15b, the next process step is Step 16: Selective removal of the hard mask layer 44;

Next, after the above step the process continues to either Step 17a-22a (single array of wires) or Step 17b-22b (stack or 3D multiple array of wires)

Option 1:

Step 17a: Placement of a top mold 46 patterned with the bottom mold pattern on top of the bottom mold;

Step 18a: Application of polymer gel 47 to the assembled mold;

Step 19a: Dry polymer 48 after water evaporation;

Step 20a: Application of additional polymer gel 49 on top of original dried polymer 48;

Step 21a: Dried polymer 50 filling the entire needle mold;

Step 22a: Demolded polymer needle with encased wires and electrodes;

Option 2:

Step 18a: Stacking of multiple bottom molds 51 and placement of a top mold 46 patterned with the bottom mold pattern on top of the bottom molds;

Step 18b: Application of multiple layers of polymer gel, followed by drying of the polymer performed until the mold is completely filled with dry polymer;

Step 22b: Demolded polymer needle with encased stacked wires and electrodes;

A detailed single-electrode probe layout with parylene tethers that hold the wiring in place during the CMC molding is shown in FIGS. 9A-C. In this particular embodiment, the meanders are set to 50 μm amplitude and 200 μm pitch. These meanders provide the axial compliance that is unique to the present invention. By including meanders, the lateral compliance is also enhanced when compared to a straight wire. For 4.5 μm-thick, 7 μm-wide, 1.5 mm long parylene electrode wiring with 50 μm amplitude and 200 μm pitch meanders, the axial spring constant is 0.35 N/m, assuming E=2.76 GPa. Lateral spring constants are below 1.1 mN/m. The platinum cross section is smaller (0.5 μm-thick, 4 μm-wide) and is for the moment neglected in this analysis. Assuming a Young's modulus of brain tissue of 30 kPa and a mechanical stress healing distance of 100 μm from the wiring, the equivalent stiffness is estimated to be 0.94 N/m acting in the axial direction on the probe described above. Therefore the equivalent brain stiffness will be larger than that of probes with this sizing (i.e., the probes will be more compliant than the brain tissue).

Multi-electrode probes will either require parylene-encased "wiring" that becomes wider as it nears the base of the shank or multiple parylene-encased wires to interconnect to multiple electrodes. Various designs are possible according to the present invention to achieve the desired compliance while being adequately tethered. Parylene is listed as a leading embodiment, but other material may be used to encase the wiring.

The shank sidewall definition is set by the sacrificial metal mask layer. A Si etch process that etches all exposed horizontal and vertical Si surfaces at an equal rate, which is called isotropic etching, undercuts the parylene/platinum wiring, tethers and tether necking regions by proceeding for a sufficient time to laterally etch the Si from under the narrow features defined by the sacrificial metal mask, but not long enough to remove the Si from under the large areas of the sacrificial metal mask. The isotropic Si etch is followed by wet etch of the sacrificial metal mask. The neck-down region of the tethers is released after the metal mask etch step as indicated in FIG. 9C. The tethers are designed to break apart upon removal of the CMC shank from the substrate.

The recording electrode size should be made as small as possible with a minimum target of 7 μm set by conservative lithography and etch. The target impedance of the electrode-solution interface is 500 kΩ at 1 kHz. The calculated 110Ω resistance of the 4 μm-wide wiring for a 1.5 mm probe is very small compared to the target electrode impedance. Even an 8 mm long probe will have resistance of only around 600Ω. Cable wiring will add to the overall device resistance but still be negligible compared to the interface resistance.

Probes according to the present invention can be made spanning a large design space, including multi-site probes, multi-probe arrays, and different probe lengths, shank widths, shank shapes, wire widths, meander widths and electrode sizes. FIGS. 10A, 10B, 11, and 12A-B are illustrations of various examples of the present invention.

Although the present invention has generally been described in terms of specific embodiments and implementations, the present invention is applicable to other methods, apparatuses, systems, and technologies. The examples provided herein are illustrative and not limiting, and other variations and modifications of the present invention are contemplated. Those and other variations and modifications of the present invention are possible and contemplated, and it is intended that the foregoing specification and the following claims cover such modifications and variations.

What is claimed is:

1. A method of spin coating fabrication of needle for a neural probe comprising:
   providing a top mold and a bottom mold to form an assembled mold with wires;
   dispensing a dissolvable material in a hydrogel form onto the assembled mold with the wires;
   centrifuging the dissolvable material to spin-cast the dissolvable material by evaporating solvent to form a dried dissolvable polymer; and
   using a wiping device with intermittent applications of water to remove excess dissolvable material to obtain needle shape only in the assembled mold with the wires to form a final dissolvable needle with wires embedded.

2. The method according to claim 1, further comprising the step of using a precision assembly approach to assemble a top mold onto a wired bottom Si mold to form the assembled with the wires.

3. The method according to claim 1, further comprising the step of using a device bonder to assemble a top mold onto a wired bottom mold to form the assembled mold with the wires.

4. The method according to claim 1, wherein the dissolvable material is carboxymethyl cellulose (CMC) or a combination of CMC and at least one of sucrose, glucose, maltodextrin, poly(vinylpyrrolidone), polyvinyl alcohol, maltose, polyactic acid.

5. The method according to claim 1, wherein the hydrogel is prepared by mixing powdered carboxymethyl cellulose (CMC) with water.

6. The method according to claim 1, wherein the solvent is water.

7. The method according to claim 1, wherein the step of centrifuging is performed at 20 deg. C at 4700 rpm spinning speed, and for 5 hours.

* * * * *